(12) United States Patent
Bucks et al.

(10) Patent No.: US 10,821,088 B2
(45) Date of Patent: *Nov. 3, 2020

(54) PAIN RELIEF COMPOSITIONS, MANUFACTURE AND USES

(71) Applicant: PROPELLA THERAPEUTICS, INC., Pittsboro, NC (US)

(72) Inventors: Daniel Bucks, Millbrae, CA (US); Philip J. Birbara, West Hartford, CT (US)

(73) Assignee: PROPELLA THERAPEUTICS, INC., Pittsboro, NC (US)

( * ) Notice: Subject to any disclaimer, the term of this patent is extended or adjusted under 35 U.S.C. 154(b) by 408 days.

This patent is subject to a terminal disclaimer.

(21) Appl. No.: 14/482,930

(22) Filed: Sep. 10, 2014

(65) Prior Publication Data

US 2016/0106690 A1 Apr. 21, 2016

Related U.S. Application Data

(62) Division of application No. 13/609,100, filed on Sep. 10, 2012, now Pat. No. 8,889,659.

(Continued)

(51) Int. Cl.
*A61K 31/4985* (2006.01)
*A61K 31/165* (2006.01)
(Continued)

(52) U.S. Cl.
CPC .......... *A61K 31/165* (2013.01); *A61K 9/0014* (2013.01); *A61K 9/06* (2013.01); *A61K 9/08* (2013.01); *A61K 31/045* (2013.01); *A61K 31/05* (2013.01); *A61K 31/125* (2013.01); *A61K 31/196* (2013.01); *A61K 31/35* (2013.01); *A61K 31/351* (2013.01); *A61K 31/352* (2013.01); *A61K 31/513* (2013.01); *A61K 31/60* (2013.01); *A61K 31/618* (2013.01); *A61K 45/06* (2013.01); *A61K 47/10* (2013.01)

(58) Field of Classification Search
CPC .............. A61K 31/4985; A61K 9/0014; A61K 31/165; A61K 9/06; A61K 45/06
See application file for complete search history.

(56) References Cited

U.S. PATENT DOCUMENTS 5,135,747 A * 8/1992 Faryniarz ................. A61K 8/11
424/401
5,145,675 A 9/1992 Won
(Continued)

FOREIGN PATENT DOCUMENTS

| EP | 0306060 | 3/1989 |
|----|---------|--------|
| JP | 60-208913 | 10/1985 |
| JP | 2008-501717 | 1/2008 |

OTHER PUBLICATIONS

Robbins et al (Anesth Analg 1998;86:579-83).*
(Continued)

*Primary Examiner* — Angela C Brown-Pettigrew
(74) *Attorney, Agent, or Firm* — Nixon & Vanderhye P.C.

(57) ABSTRACT

The present invention relates to TRPV1 selective agonist topical compositions including capsaicinoid and analgesic agent compositions and methods of manufacture and methods of providing pain relief as well as treating a variety of disorders with such compositions.

31 Claims, 5 Drawing Sheets

API-CAPS TOLERABILITY

Related U.S. Application Data

(60) Provisional application No. 61/533,120, filed on Sep. 9, 2011, provisional application No. 61/642,942, filed on May 4, 2012.

(51) Int. Cl.

| | | |
|---|---|---|
| *A61K 31/045* | (2006.01) | |
| *A61K 31/05* | (2006.01) | |
| *A61K 31/125* | (2006.01) | |
| *A61K 31/618* | (2006.01) | |
| *A61K 31/351* | (2006.01) | |
| *A61K 31/60* | (2006.01) | |
| *A61K 9/00* | (2006.01) | |
| *A61K 47/10* | (2017.01) | |
| *A61K 9/08* | (2006.01) | |
| *A61K 31/35* | (2006.01) | |
| *A61K 31/513* | (2006.01) | |
| *A61K 45/06* | (2006.01) | |
| *A61K 31/352* | (2006.01) | |
| *A61K 9/06* | (2006.01) | |
| *A61K 31/196* | (2006.01) | |

(56) References Cited

U.S. PATENT DOCUMENTS

| | | | | |
|---|---|---|---|---|
| 5,665,378 | A * | 9/1997 | Davis | A61K 9/7061 424/447 |
| 6,593,370 | B2 * | 7/2003 | Tamura | A61K 31/165 424/400 |
| 7,282,224 | B1 | 10/2007 | Roederer | |
| 2006/0100272 | A1 * | 5/2006 | Maniar | A61K 31/045 514/485 |
| 2006/0148903 | A1 | 7/2006 | Burch et al. | |
| 2009/0098173 | A1 * | 4/2009 | Robinson | A61K 8/02 424/402 |

OTHER PUBLICATIONS

Wu et al (International Journal of Pharmaceutics 222 (2001) 225-235).*
Racz et al (Techniques of Neurolysis, 1989) (Year: 1989).*
Mason et al (BMC Musculoskeletal Disorders 2004, 5:28) (Year: 2004).*
Niazi, S. K. (2004). Handbook of pharmaceutical manufacturing formulations. Semisolid Products (vol. 4). New York, NY: Informa Healthcare (Year: 2004).*
Examination Report for Application No. 12 766 516.4 dated Dec. 22, 2015.
Office Action issued in European Application No. 12 766 516.4 dated Mar. 31, 2015.
Dailymed, Apanol Linimento Obrero (methyl salicylate, capsaicin) ointment [Delon Laboratories (1990) Ltd].
Dailymed, Salonpas Pain Relieving (camphor, menthol, methyl salicylate) patch [Hisamitsu Pharmaceutical Co., Inc.], Jul. 2012.
IPRP and Written Opinion for PCT/US2012/054511, dated Mar. 12, 2014.
Ohta et al., Involvement of Transient Receptor Potential Vanilloid Subtype 1 in Analgesic Action of Methylsalicylate, Molecular Pharmacology, 2009, vol. 75, No. 2, pp. 307-317.
Martin et al., Dermal absorption of camphor, menthol, and methyl salicylate in humans., J Clin Pharmacol., 2004, vol. 44, No. 10, pp. 1151-1157.
International Search Report and Written Opinion dated Nov. 22, 2012 issued in connection with PCT/US2012/054511, filed Sep. 10, 2012.
"Medicines/Drugs", MedGuideIndia.com, 2010, XP002687143, Retrieved from the Internet: URL:http://www.medguideindia.com/find_brand_bygeneric.php?gen_mask=,18,21,42,672,1605,2509 [retrieved on Nov. 14, 2012] the whole document.
"Muscular balm", Drugs.com, 2010, XP002687144, Retrieved from the Internet: URL:http://www.drugs.com/otc/105589/muscular-balm.html [retrieved on Dec. 13, 2012], first page, section "active ingredients".
Agarwal et al, "Comparative evaluation of myolaxin and EMLA cream for attenuation of venous cannulation pain: a prospective, randomised, double blind study", The free library, Oct. 1, 2007, XP002687145, Retrieved from the Internet: URL:file:///C:/Documents%20and%20Settings/td51778/Desktop/Emla%20cream.htm [retrieved on Nov. 14, 2012], second of methods; last of results.
Pao-Chu Wu et al, "Evaluation of percutaneous absorption and skin irritation of ketoprofen through rat skin: in vitro and in vivo study", International Journal of Pharmaceutics 222(2):225-235 (2001).
Green et al, "Menthol desensitization of capsaicin irritation: Evidence of a short-term anti-nociceptive effect", Physiology & Behavior 68(5):631-639 (2000).
Xu et al, "Camphor Activates and Strongly Desensitizes the Transient Receptor Potential Vanilloid Subtype 1 Channel in a Vanilloid-Independent Mechanism", The Journal of Neuroscience 25(39):8924-8937 (2005).
Jintu, Axe Brand Red Flower Oil, http://www.itmonline.org/jintu/redflower.htm.
OrientalPharmacy.com, Chinese Medicine Distributor, Red Flower Pain Relieving Oil: Zheng Hong Hua (S79): OS, http://www.orientalpharmacy.com/redflpareoil.html.
61734-203-01: Apanol, http://www.hipaaspace.com/Medical_Billing/Coding/National.Drug.Code . . . .
Ultra Strength Bengay® Cream, http://www.bengay.com/bengay-ultra-strength-cream.
Eagle Brand Muscular Balm External Analgesic, http://dailymed.nlm.nih.gov/dailymed/lookup.cfm?setid=ed79fl4e-6b3d-4 . . . .
Myolaxin-D Gel, http://www.genopharma.com/home.php?prodid=25&thid=3.
Pain Relief Roll on Roll on (methyl salicylate mentol camphor capsaicin) liquid, http://dailymed.nlm.nih.gov/dailymed/drugInfo.cfm?id=26781.
Macpherson et al, "More than cool: Promiscuous relationships of menthol and other sensory compounds", Mol. Cell. Neurosci. 32:335-343 (2006).
Mason et al. (BMJ, doi:10.1136/bmj.38042.506748.EE (published Mar. 19, 2004).
Ong et al. Clinical Medicine & Research vol. 5, No. 1: 19-34.
Agarwal, A., et al. "Comparative evaluation of Myolaxin and EMLA cream for attenuation of venous cannulation pain: A prospective, randomized, double blind study" Anaesthesia and Intensive Care vol. 35, No. 5, pp. 726-729, 2007.
Wu, Pao-Chu, "Evaluation of percutaneous absorption and skin irritation of ketoprofen through rat skin: in vitro and in vivo study" Int'l Jnl. Of Pharm 222:225-235, 2001.
Korean Office Action in Korean Patent Application No. 2014-7008331, dated Oct. 20, 2015 and English translation.
Korean Office Action issued in App. No. 10-2014-7008331 dated Oct. 13, 2016 (w/ translation).
Mexican Office Action issued in App. No. MX/a/2014/002718 dated Oct. 21, 2016 (w/ English Summary).
Japanese Office Action issued in App. No. 2014-529957 dated Jun. 6, 2016 w/ translation.
Search Report issued in EP Appln. No. 18161847.1 dated Sep. 19, 2018.

* cited by examiner

FIGURE 3 – API-CAPS, 0.25% CAPSAICIN, EFFICACY IN OSTEOARTHRITIC PAIN MANAGEMENT

FIGURE 4 – API-CAPS, 0.25% CAPSAICIN, TOLERABILITY

PAIN RELIEF COMPOSITIONS, MANUFACTURE AND USES

This application is a divisional of U.S. application Ser. No. 13/609,100, filed Sep. 10, 2012, now U.S. Pat. No. 8,889,659, which claims priority from U.S. Provisional Application No. 61/533,120, filed Sep. 9, 2011 and U.S. Provisional Application No. 61/642,942, filed May 4, 2012, the entire contents of each of which are incorporated herein by reference.

FIELD OF THE INVENTION

The present invention relates to compositions of transient receptor potential vanilloid 1(TRPV1) selective agonists such as capsaicin, and related compounds, methods of manufacture and methods of providing pain relief, as well as methods of treating a variety of medical conditions.

BACKGROUND OF THE INVENTION

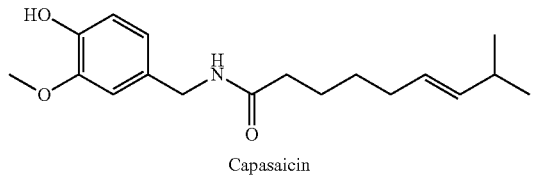 [SMILES: COc1cc(CNC(=O)CCCC/C=C/C(C)C)ccc1O]

Capasaicin

Capsaicin is the main capsaicinoid in *capsicum* plants including chili peppers. It is a pungent substance that has long been used for the relief of pain because of its selective action on the small diameter afferent nerve fibers (C fibers and A-delta fibers) that are believed to signal pain. From studies in animals, capsaicin appears to trigger C fiber membrane depolarization by opening cation channels permeable to calcium and sodium.

Capsaicin has been reported to work by depleting a compound called Substance P, which is a neuropeptide that functions as a neurotransmitter and promotes pain perception, from the nerve terminal fibers. However, capsaicin also can elicit erythema and/or an intense burning or stinging sensation upon application. The intense burning or stinging can be intolerable for some. Additionally, it may take more than a day or two for effectuating actual pain relief, and for the intense burning to stop. Following the initial period of intense burning pain that may be accompanied by erythema, topical capsaicin application causes insensitivity to pain elicited by a variety of noxious stimuli or disease states. In theory, neurons shut down after they've been stimulated by capsaicin, so the burning and other unrelated sensations—including pain—cease. The results from studies testing the low concentrations of capsaicin present in most over-the-counter products (0.075 percent or less) haven't been impressive. Many people are bothered by the burning sensation, so they don't stick with the treatment. Current over-the-counter capsaicin products are not effective for many people. High-dose capsaicin patches have been developed, but they require local or regional anesthesia and therefore are only appropriate for treatment for severe chronic pain under the supervision of a physician.

Because of the ability of capsaicin to desensitize nociceptors in peripheral tissues, their potential analgesic effects have been assessed in various clinical trials. However, since the application of capsaicin itself frequently causes burning pain and hyperalgesia apart from the neuropathic pain being treated, patient compliance has been poor and the drop-out rates during clinical trials have typically exceeded fifty percent. The most frequently encountered adverse effect with capsaicin is burning pain at the site of application, particularly in the first week of application. This can make it impossible to blind trials and can lead to dropout rates ranging from 33 to 67% (Watson C P et al. "*A randomized vehicle-controlled trial of topical capsaicin in the treatment of postherpetic neuralgia.*" Clinical Therapeutics. 15.3 (1993):510-26.) Another factor in compliance is the time delay before therapeutic effect is observed. Daily topical applications for at least a week or two may be required.

Many individuals discontinue the prolonged treatment of topical capsaicin prior to the anticipated analgesic effects of capsaicin due to the intense stinging and burning pain. It was reported that 26 out of 39 (66.7%) patients suffering from post-herpetic neuralgia did not tolerate the treatment of a 0.025% capsaicin preparation (Zostrix, Gen Derm, USA). With a 0.075% preparation (Zostrix-HP, Gen Derm, USA), 5 out of 16 (31.3%) and 45 out of 74 (60.8%) patients with post-herpetic neuralgia did not tolerate the long term topical treatment. (Peikert, A. et al., *Topical 0.025% capsaicin in chronic post-herpetic neuralgia: efficacy, predictors of response and long-term course, J. Neurol.* 238:452-456, 1991; Watanabe, A. et al., *Efficacy of capsaicin ointment (Zostrix) in the treatment of herpetic pain and postherpetic neuralgia, Pain Clinic* 15:709-713, 1994; Bernstein J. E. et al., *Topical capsaicin treatment of chronic postherpetic neuralgia, J. Am. Acad. Dermatol.* 21: 265-270, 1989; and Watson C. P. N. et al., *A randomized vehicle-controlled trial of topical capsaicin in the treatment of postherpetic neuralgia, Clin. Ther.* 15:510-526, 1993.)

The spontaneous burning pain and hyperalgesia are believed to be due to intense activation and temporary sensitization of the peripheral nociceptors at the site of capsaicin application. This activation and sensitization occurs prior to the desensitization phase and is a barrier to topical capsaicin use because the burning pain produced compromises patient's tolerability of treatment.

Capsaicin is believed to relieve pain by causing a localized degradation of the C neuron endings. The activity of capsaicin results from its binding to, and activating, an ion channel called vanilloid receptor 1, or VR1. Under normal circumstances, when the VR1 ion channel is activated, it opens for a short time, causing the C neurons to transmit a pain signal toward the brain. When capsaicin binds to, and activates VR1, it causes a series of events within the cell that degrade the pain-sensing endings, or terminals of the C neuron, thereby preventing the neuron from transmitting pain signals.

In 1997, a research team led by David Julius of University of California, San Francisco showed that capsaicin selectively binds to a protein known as TRPV1 that resides on the membranes of pain and heat sensing neurons TRPV1 is a heat activated calcium channel, which opens between 37 and 45° C. (98.6 and 113° F., respectively). When capsaicin binds to TRPV1, it causes the channel to open below 37° C. (normal human body temperature), which is why capsaicin is linked to the sensation of heat. Prolonged activation of these neurons by capsaicin depletes presynaptic substance P, one of the body's neurotransmitters for pain and heat. Neurons that do not contain TRPV1 are unaffected. The result appears to be that the chemical mimics a burning sensation; the nerves are overwhelmed by the influx, and are unable to report pain for an extended period of time. With chronic exposure to capsaicin, neurons are depleted of neurotransmitters, leading to reduction in sensation of pain and blockade of neurogenic inflammation. If capsaicin is removed, the neurons recover.

Although capsaicin's analgesic effect was thought to be due to a depletion in the pain-causing substance P, recent evidence suggests a process of "defunctionalization" of nociceptor fibers is responsible for its analgesic effect. (Anand P, Bley K. *Topical capsaicin for pain management: therapeutic potential and mechanisms of action of the new high-concentration capsaicin 8% patch. Br J Anaesth.* 2011; 107(4):490-502.)

Humans have long been exposed to dietary sources of capsaicin-containing spices and to topical preparations used for a variety of medical indications. This vast experience has not revealed significant or lasting adverse effects of capsaicin exposure. The recent determination of potential therapeutic effects of capsaicin on unmyelinated sensory afferent nerve fibers requires diligent consideration of this compound for further pharmaceutical development.

Capsaicin is currently marketed for topical administration in the form of over-the-counter, low dose, non-sterile creams and patches, which tend to be poorly absorbed. There are more than thirty brands of creams and patches, including Capzasin-P® (Chattem) and Zostrix® (Rodlen Laboratories). These over-the-counter preparations can be purchased widely without a prescription and are used topically by consumers to relieve pain with variable and often inadequate results in conditions such as osteoarthritis, shingles (herpes zoster), psoriasis and diabetic neuropathy.

In addition to relieving pain, capsaicin triggers the body to increase blood flow to promote natural healing on the skin surface and within the epidermal layers. This is especially important for healing injuries and environmental damage from pollution, sun and winter weather. Capsaicin is also a powerful anti-microbial that destroys bacteria in clogged skin pores and hair follicles.

Topical capsaicin has been used in skin and scalp care products that target a variety of conditions including acne, dermatitis, eczema, psoriasis and even dandruff. Capsaicin can stop itching when topically applied. Known in the medical world as pruritus, itching is both a symptom and a cause of many skin ailments. The more a person itches, the more they scratch and the worse their condition becomes. Unfortunately, many skin and scalp conditions cause itching that leads to a chronic cycle of sick skin. From bug bites to eczema, the key to fast healing is to stop the itch so the condition can heal naturally, and capsaicin is a known natural substance that can effectively do this.

Capsaicin mediated effects include: (i) activation of nociceptors in peripheral tissues; (ii) eventual desensitization of peripheral nociceptors to one or more stimulus modalities; (iii) cellular degeneration of sensitive A-delta and C-fiber afferents; (iv) activation of neuronal proteases; (v) blockage of axonal transport; and (vi) the decrease of the absolute number of nociceptive fibers without affecting the number of non-nociceptive fibers.

The use of capsaicin is known for the treatment of a number of pain disorders. Accordingly, topical preparations of capsaicin find use as a topical therapy for a variety of skin disorders that involve pain and itching, such as postherpetic neuralgia, diabetic neuropathy, pruritus, psoriasis, cluster headache, postmastectomy pain syndrome, rhinopathy, oral mucositis, cutaneous allergy, detrusor hyperreflexia, loin pain/hematuria syndrome, neck pain, amputation stump pain, reflex sympathetic dystrophy, pain due to skin tumor and arthritis including rheumatoid arthritis, osteoarthritis, diabetic neuropathy, psoriasis, pruritus (itching), cluster, headache, post-surgical pain, oral pain, and pain caused by injury, amongst others. (Martin Hautkappe et al., *Review of the Effectiveness of Capsaicin for Painful Cutaneous Disorders and Neural Dysfunction, Clin. J. Pain,* 14:97-106, 1998)

Capsaicin is used in topical ointments and creams to relieve minor aches and pains of muscles and joints. Capsaicin is also available in large adhesive bandages that can be applied to the back. Concentrations of capsaicin are typically between 0.025 wt. % and 0.075 wt. %. A partial listing of capsaicin products with their capsaicin, methyl salicylate, camphor, and menthol contents is shown below in Table 1.

TABLE 1

| Product Name | % Capsaicin | % Methyl Salicylate | % Camphor | % Menthol |
| --- | --- | --- | --- | --- |
| APANOL LINIMENTO OBRERO | 10% | 27% | — | — |
| Axane* | 0.025% | 5% | 2.5% | 2.5% |
| Axe Brand Red Flower Oil | 0.25% | 60% | — | — |
| Capzasin-P and Capzasin-HP | 0.035% | — | — | — |
| CORALITE TOPICAL ANALGESIC) liquid | 0.025% | Inactive | Inactive | — |
| DENDRACIN NEURODENDRAXCIN lotion | 0.025% | 30% | — | 10% |
| DENDRACIN NEURODENDRAXCIN lotion | 0.0375% | 30% | — | 10% |
| DR. OH BALM) cream | 0.015% | — | 3.5% | 1% |
| EXOTEN-C Lotion | 0.002% | 20% | — | 10% |
| Heet Pain Reliever with Hand's Off Applicator | 0.025% | 18% | 3.6% | — |
| ICY HOT ARTHRITIS lotion | Inactive | — | 4% | 16% |
| MEDI-DERM TOPICAL PAIN RELIEF cream | 0.035% | 20% | — | 5% |
| MEDROX ointment | 0.0375% | 20% | — | 5% |
| MEDROX-RX ointment | 0.050% | 20% | — | 7% |
| (Bordon/Eagle) MUSCULAR BALM ointment | 0.15% | 30% | — | 13.5% |
| Myolaxin-D Gel | 0.075% | 20% | 5% | 10% |
| ORTHO-NESIC WITH CAPSAICIN gel | 0.01% | — | 0.2% | 3/5% |
| OVERTIME lotion | 0.0375% | 30% | — | 10% |
| PAIN RELIEFROLL ON ROLL ON | 0.03% | 30% | 4% | 10% |
| TEROCIN lotion | 0.025% | 25% | — | 10% |
| TOPICAL PAIN RELIEF cream | 0.035% | 20% | — | 5% |
| XOTEN-C lotion | 0.002% | 20% | — | 10% |
| ZIKS ARTHRITIS PAIN RELIEF cream | 0.025% | 12% | — | 1% |
| Zostrix | 0.025% | — | — | — |
| Zostrix-HP | 0.075% | — | — | — |

One approach toward potentially minimizing adverse effects and accelerating the rate of analgesia has been to topically apply a higher capsaicin concentration as practiced by the Qutenza® (capsaicin) 8% patch under regional anesthesia. Application of the Qutenza® (capsaicin) 8% patch provides for sustained analgesia lasting 1 to 8 weeks in cases of complex regional pain syndrome and neuropathic pain (Robbins et al. *Treatment of intractable pain with topical large-dose capsaicin: preliminary report. Anesth. Analg.* 1998; 86:579-583). When topical local anesthetics were applied with 1% topical capsaicin, no alteration in pain produced by the capsaicin was observed in healthy subjects indicating that this co-treatment approach was not sufficient to block the pain induced by capsaicin (Fuchs et al., *Secondary hyperalgesia persists in capsaicin desensitized skin. Pain* 2000; 84: 141.)

Analgesics

The primary use of a topical analgesic is to relieve the pain such as that associated with arthritis as well as muscle aches and pains caused by sports injuries or physical work. One benefit of topical pain relievers is that they can be applied directly to the site of the pain, so there is minimal systemic distribution of the pain reliever throughout the body. This localized application and associated action minimizes the potential for systemic side effects. In addition, the pain relieving action of topical analgesics is faster than most oral forms because it is applied directly onto the painful area whereas oral analgesics need to be digested, absorbed in the gastrointestinal tract, survive first-pass metabolism in the liver and then be transported throughout the body.

Methyl Salicylate

Methyl salicylate (oil of wintergreen or wintergreen oil) is a natural product of many species of plants. Some of the plants which produce it are called wintergreens, hence the common name. Methyl salicylate is an analgesic.

Methyl salicylate is an active ingredient in many over-the-counter pain-relief ointments. It is one of a group of anti-inflammatory chemicals known collectively as salicylates because salicylic acid is their shared, root compound. Aspirin—salicylic acid with an acetyl group attached (thus its formal chemical name, acetylsalicylic acid)—is the best known of the salicylates.

Topical analgesics containing methyl salicylate suppress pain by blocking the enzymes involved in the production of prostaglandins, which signal inflammation and cause pain. The health benefits of wintergreen oil are in the analgesic, anti rheumatic, anti spasmodic and astringent properties it contains. The oil is said to relieve pain by way of the methyl salicylate compound, which causes the treated, affected area of the body to experience a feeling of numbness, to help with blood circulation and to promote a warming in the affected area. The mechanism of action by which methyl salicylate expresses topical analgesia is not fully understood. Current literature indicates that methyl salicylate has both stimulatory and inhibitory actions on TRPV1 channels and suggests that the latter action may partly underlie the analgesic effects of methyl salicylate independent of inhibition of cyclooxygenases in vivo. In addition, methyl salicylate-induced human TRPV1 activation was mediated by distinct channel regions from capsaicin. (*Mol Pharmacol.* 2009 February; 75(2):307-17. Epub 2008 Nov. 5.)

Menthol

Menthol is an organic compound made synthetically or obtained from peppermint or other mint oils. The natural form of menthol ((l)-menthol) exists as one pure stereoisomer and is the preferred form for analgesic effects.

Menthol's ability to chemically trigger the cold-sensitive TRPM8 receptors in the skin is responsible for the well-known cooling sensation that it provokes when inhaled, eaten, or applied to the skin. Menthol has analgesic properties that are mediated through a selective activation of κ-opioid receptors. Typically, ice is applied to the skin to create a cold response in order to reduce pain because cold reduces the pain threshold. Menthol creates a chemical action on cold receptors rather than a physical action, resulting in a cold response. Patel and colleagues provide an excellent review of the mechanisms behind menthol. (Patel T, Ishiuji Y, Yosipovitch G. *Menthol: a refreshing look at this ancient compound. J Am Acad Dermatol.* 2007; 57(5): 873-878.)

Similar to ice, topical application of menthol in a 3.5% gel reduces blood flow by 35% within 60 seconds of application, and remains ~20% reduced at 10 minutes after application. (Olive J L, Hollis B, Mattson E, Topp R. *Vascular conductance is reduced after menthol or cold application. Clin J Sport Med.* 2010; 20(5):372-376). Recently, Topp and colleagues noted decreased blood flow in both lower limbs after application to one limb, suggesting a possible systemic mechanism of topical menthol. (Topp R, Winchester L J, Schilero J, Jacks D. *Effect of topical menthol on ipsilateral and contralateral superficial blood flow following a bout of maximum voluntary muscle contraction. Int J Sports Phys Ther.* 2011; 6(2):83-91.)

Studies have shown that (l)-menthol (natural menthol derived from peppermint oil) was able to increase pain threshold whereas (d)-menthol (synthetic menthol) was completely devoid of any analgesic effect.

Menthol is an active ingredient in most of the traditional rub-in products that elicit a cooling sensation.

Camphor

Camphor is a naturally occurring compound that is used as a major active ingredient of balms and liniments supplied as topical analgesics. Camphor is highly volatile and readily absorbed through the skin. It produces a cool sensation and can under certain circumstances act as a mild local anesthetic. Camphor is readily absorbed through the skin and produces a feeling of cooling similar to that of menthol, and can act as a local anesthetic substance. There are anti-itch and cooling gels with camphor as the active ingredient.

When applied externally, camphor can numb the nerve endings. The nerve endings then no longer transmit the sensation of pain. Camphor has recently been shown to activate TRPV3, and it has been demonstrated that camphor also activates heterologous expressed TRPV1, requiring higher concentrations than capsaicin. The camphor-induced desensitization of TRPV1 and block of TRPA1 may underlie the analgesic effects of camphor.

Camphor oil was traditionally massaged into sprains and sore muscles and joints for pain relief, and most modern herbalists agree that this is the best use for pure camphor oil. Camphor has been shown to help ease inflammation. It is readily absorbed when applied topically, making it a particularly effective treatment for arthritic and rheumatic joint pain.

Phenol

Phenol is fairly widely used as a topical antiseptic agent in sore throat lozenges and sprays and as well as a topically applied skin exfoliant. Small amounts of phenol are present in many consumer products that are commonly used, such as mouthwashes, sore throat lozenges, ear or nose drops, cold sore lotions, analgesic rubs and antiseptic lotions. Phenol is the active ingredient in the marketed oral analgesics Chloraseptic spray and Carmex.

Campho-Phenique, a commonly used topical OTC product, contains the active ingredients 10.8% camphor, 4.7% phenol blended with the *eucalyptus* and mineral oil. ingredients. The combination of camphor with phenol has been cited for its anesthetic and antiseptic properties.

Other Natural Analgesic Ingredients

In addition to methyl salicylate, menthol, camphor and phenol, ingredients with analgesic properties possessing analgesic and other desirable therapeutic properties include eugenol, thymol and several essential oils.

Eugenol, a component of clove oil and some essential oils, has analgesic, anti-inflammatory, and antibacterial effects. It is also used as a flavoring agent and is used in oral hygiene preparations e.g. mouthwash. Eugenol can also be mixed with other pain reducing products to increase the pain relief.

Thymol is an essential oil found in several species of thyme and oregano plants that contains significant antibacterial, antifungal, antiseptic, analgesic and antioxidant properties.

There are many analgesic compositions on the market for topical application and the specific compositions of several of them are presented in Table II. The molecular structures of several of the analgesic ingredients are shown in FIG. 5.

TABLE II

EXTERNAL ANALGESIC COMPOSITIONS

| | White Flower Oil | Po Sum on Medicated Oil | Koong Yic (Hong Hoa Oil) | Wood Lock Oil | Shilling Oil | Eagle Brand Medicated Oil | Kwan Loong Oil |
|---|---|---|---|---|---|---|---|
| Camphor | 6 | | | 16 | 5 | | |
| Menthol Oil | 15 | | | 10 | 16 | 14.5 | 16 |
| Methyl Salicylate | 40 | | 66 | 50 | 47 | 30 | 35 |
| Lavender Oil | 6 | | | | — | | 7 |
| Eucalyptus Oil | 18 | | | | — | | 3 |
| Peppermint Oil | 15 | 57.3 | | | | | |
| Tea Oil | | 38.7 | | | | | |
| Dragon Blood | | 2.07 | | | | | |
| Cinnamon Oil | | 0.96 | — | | | | |
| Licorice | | — | | | | | |
| Turpentine Oil | | | 22 | | | | |
| Clove Oil | | | — | | | | |
| EtOH | | | | | | 13 | |
| Chlorophyll | | | | | | — | |
| Dill Oil | | | | | — | | |
| Mineral Oil | | | | | | — | 39 |

NSAIDs

NSAIDs decrease pain, inflammation, and fever by blocking cyclooxygenase (COX) enzymes. Understanding of the pharmacology of NSAIDs continues to evolve, but it is now thought that most NSAIDs block three different COX isoenzymes, known as COX-1, COX-2, and COX-3. COX-1 protects the lining of the stomach from acid. COX-2 is found in joint and muscle, and mediates effects on pain and inflammation. By blocking COX-2, NSAIDs reduce pain compared to placebo in patients with arthritis, low back pain, minor injuries, and soft tissue rheumatism. However, NSAIDs that also block the COX-1 enzyme (also called "nonselective NSAIDs") can cause gastrointestinal bleeding.

Clinical trials have demonstrated that topical NSAIDs have a better safety profile than oral NSAIDs. Adverse effects secondary to topical NSAID use occurs in about 10 to 15% of patients and are primarily cutaneous (rash and pruritus where the topical NSAID was applied). Gastrointestinal adverse drug reactions are rare with topical NSAIDs, compared with a 15% incidence reported for oral NSAIDs. Hayneman, C. et al, *Oral versus topical NSAIDs in rheumatic diseases: a comparison, Drugs*, pgs. 555-74, September, 2000.

Several topical formulations combine NSAIDS, primarily diclofenac salts, with capsaicin. The Table below contains a listing of several of these formulations.

| Topical Formulations Containing Capsaicin & Diclofenac Salts | | | |
|---|---|---|---|
| ITEM NO. | TRADE NAME | ACTIVE INGREDIENTS | COMPANY |
| 1 | Topac Fast | Gel; Topical; Capsaicin 0.025%; Diclofenac Sodium 1%; Menthol 5%; Methyl Salicylate 5% | Abbott |
| 2 | Voveran Thermagel | Gel; Topical; Capsaicin 0.025%; Diclofenac Sodium 1%; Menthol 5%; Methyl Salicylate 5% | Novartis |
| 3 | Xidol Gel | Gel; Topical; Capsaicin 0.025%; Diclofenac Diethylamine 1.16%; Linseed Oil 3%; Menthol 5%; Methyl Salicylate 10% | Dewcare Concept |
| 4 | Diclomax Power | Gel; Topical; Capsaicin 0.025%; Diclofenac Diethylamine 1.16%; Linseed Oil 3%; Menthol 5%; Methyl Salicylate 10% | Torrent Pharmaceuticals |
| 5 | Divexx Gel | Gel; topical; Capsaicin 0.022%; Diclofenac Sodium 1%; Menthol 5%; Methyl Salicylate 10% | Zuventus Healthcare |

U.S. Pat. No. 4,424,205 discloses a variety of hydroxyphenylacetamides having analgesic and anti-irritant properties.

U.S. Pat. No. 4,486,450 discloses a method and composition of treating psoriatic skin in which capsaicin is applied topically to the psoriatic skin in a pharmaceutically acceptable carrier wherein capsaicin is present in therapeutically acceptable concentrations of between about 0.01 and about 1 percent by weight. Subsequent exposure of the treated psoriatic skin to ultraviolet light in small doses aids treatment.

U.S. Pat. No. 4,997,853 discloses a method and composition for treating superficial pain syndromes, which incorporates capsaicin into a pharmaceutically acceptable carrier, and adding to this composition a local anesthetic such as lidocaine or benzocaine. The composition containing the anesthetic is then applied to the site of the pain. A variation on the treatment includes initial treatment with the composition containing the local anesthetic until the patient has become desensitized to the presence of capsaicin and subsequent treatment with a composition omitting the local anesthetic.

U.S. Pat. No. 5,134,166 discloses methods and compositions for treating certain allergy related condition and headaches using capsaicin in solution or suspension combined with a selected anesthetic, topical steroid or antihistamine.

U.S. Pat. No. 5,178,879 discloses clear, water-washable, non-greasy gels useful for topical pain relief containing capsaicin, water, alcohol and a carboxypoly-methylene emulsifier. A method of preparing the gels is also disclosed.

U.S. Pat. No. 5,560,910 discloses compositions and methods that are useful for topically treating inflammation caused by a wide variety of diseases. The compositions comprise an effective amount of a proteolytic enzyme, such as bromelain, in combination with capsaicin in a pharmaceutically acceptable carrier.

U.S. Pat. No. 5,910,512 discloses a water-based topical analgesic and method of application wherein the analgesic contains *capsicum, capsicum* oleoresin and/or capsaicin. This analgesic is applied to the skin to provide relief for rheumatoid arthritis, osteoarthritis, and the like.

U.S. Pat. No. 5,962,532 discloses a method of providing pain relief comprising administering an anesthetic along with injecting a composition of capsaicin.

U.S. Pat. No. 6,239,180 discloses a transdermal application of capsaicin in a concentration from greater than about 5 wt. % to about 10 wt. % for treating neuropathic pain. An anesthetic is initially administered to minimize the burning side effects from subsequent capsaicin application.

U.S. Pat. No. 6,348,501 discloses a lotion for treating the symptoms of arthritis using capsaicin and an analgesic along with a method for making such formulations.

U.S. Pat. No. 6,573,302 discloses a cream comprising: a topical carrier wherein the topical carrier comprises a member selected from the group comprising lavender oil, myristal myristate, and other preservatives in addition to *hypericum perforatum arnica montana* capric acid; and 0.01 to 1.0 wt. % capsaicin; 2 to 10 wt. % of an encapsulation agent selected from the group comprising colloidal oatmeal hydrogenated lecithin, dipotassium glycyrlhizinate and combinations thereof; esters of amino acid; a light scattering element having a particle size up to 100 nm.; and a histidine.

U.S. Pat. No. 6,593,370 discloses a topical capsaicin preparation for the treatment of painful cutaneous disorders and neural dysfunction. The preparation contains a nonionic, amphoteric or cationic surfactant in an amount effective to eliminate or substantially ameliorate burning pain caused by capsaicin.

US Patent Application 2005/0090557 relates to compositions of a TRPV1 agonist such as capsaicin, and a solvent system such as a penetration enhancer.

U.S. Patent Application 2006/0100272 discloses compositions and methods for the treatment of pain, and neuropathic pain in particular. The formulations are eutectic mixtures of a capsaicinoid and a local anesthetic agent and/or an anti-pruritic agent.

US Patent Application 2006/0148903 relates to a method of treating post surgical pain comprising administering at the surgical site, a dose of capsaicinoid gel.

U.S. Pat. No. 7,282,224 discloses a pain relief composition comprising an effective amount of a nerve inhibiting component, including capsaicin, a capsaicinoid or a capsaicin analogue, which numbs or inhibits the nerve endings that signal pain, in combination with at least one of the following: an effective amount of an inflammation control component which is designed to reduce immediate pain and discourage future pain in the joints and muscles; an effective amount of a cooling component; an effective amount of a heat minimizing or blocking component; an effective amount of a circulation increasing component which effectuates better penetration of the actives to the skin and nerves; and an effective amount of a soothing and anti-inflammatory complex for the joints and/or muscles comprising glucosamine sulfate or HCl, *zingiber officiniale* (ginger root) extract, methyl sulfonylmethane (MSM), *polygonum cuspidatum*.

U.S. Pat. No. 7,632,519 discloses a variety of TRPV1 agonist compounds (capsaicinoids and their related esters) and formulations thereof.

U.S. Pat. No. 7,771,760 discloses topical oils of capsaicinoids comprising a capsaicinoid, a solvent capable of solubilizing the capsaicinoid, and a capsaicinoid crystallization inhibitor.

U.S. Pat. No. 7,943,166 relates to a method and liquid solvent system of penetration enhancers from 10% (w/v) to about 30% (w/v) of a TRPV1 agonist, such as capsaicin, where a single topical application of the liquid formulation results in pain relief for at least two weeks.

U.S. Pat. No. 7,943,666 discloses formulations of ester derivatives of capsaicin and ester derivatives of myristoleic acid. These derivatives are capable of reverting to the active parent compound following enzymatic or chemical hydrolysis. These derivatives have a higher lipophilicity, lipid solubility and less irritation to the skin than the parent compound, and hence are better able to be incorporated into certain pharmaceutical formulations, including cream and ointment pharmaceutical formulations. The disclosed pharmaceutical compositions are useful for pain management in mammals in vivo and have been contemplated to be used in the treatment of various pains in humans.

Despite the advancements in the art, there remains a need for more effective pain-relieving capsaicin formulations.

OBJECTS OF THE INVENTION

It is an object of the invention to provide a topical pain relief composition that provides long-term pain relief without loss of sensation in the area treated.

It is an object of the invention to provide topical compositions of TRPV1 selective agonists such as capsaicin and other related compounds in preparations which eliminate or substantially ameliorates initial burning/stinging pain caused by the TRPV1 selective agonist compound observed following topical administration thereby making the preparation tolerable following initial and long-term use.

It is an object of the invention to provide topical TRPV1 selective agonist containing compositions such as capsaicin formulations for use in the treatment of joint pain, tendonitis, and for certain forms of localized neuropathic pains that are not amenable to treatment with currently marketed topical preparations, and do not have the side effects of systemic treatments.

It would be advantageous to provide methods and compositions containing compositions such as capsaicin or analogues thereof, at therapeutically effective concentrations to cause an analgesic effect without the side effects normally associated with the use of capsaicin.

It is therefore an object of the present invention to provide methods for administering capsaicin or capsaicin analogues topically at high concentrations to achieve a prolonged pain reduction effect but without the severe burning sensation that occurs following topical application.

It is yet another object of the present invention to provide compositions containing analgesic/anti-inflammatory agents to complement the remedial properties of capsaicin, or related compounds, for the treatment of pain of the joints and muscles and other medical conditions, where the analgesic agents are conveniently administered with the capsaicin.

It is yet another object of the present invention to provide a composition and method for topically treating pain and inflammation that is safe and effective and does not have the side effects of conventional NSAIDS.

It is another object of this invention to provide solvent systems that solubilize appreciable concentrations of the relatively aqueous insoluble TRPV1 selective agonists (such as capsaicin and capsaicin derivatives) to produce compositions such that solvent systems contains analgesic and anti-inflammatory ingredients that rapidly penetrate the skin's layers to mitigate the stinging and burning pain resulting from the topical application of the significant capsaicin concentrations.

Other objects and advantages of the present invention will be apparent from a review of the following specification.

SUMMARY OF THE INVENTION

The invention relates to liquid solution compositions comprising a TRPV1 selective agonist, and an analgesic agent capable of solubilizing said TRPV1 selective agonist, wherein said composition has an amount of TRPV1 selective agonist sufficient to decrease the density of functional nociceptive nerve fibers when said composition is applied topically, and said composition has an amount of analgesic agent sufficient to eliminate or reduce the burning sensation or erythema created by the topical administration of the TRPV1 specific agonist. In one embodiment, the amount of TRPV1 selective agonist sufficient to decrease the density of functional nociceptive nerve fibers by at least 20%, or at least 50%, after topical application.

In another embodiment the composition is 0.20-30% by weight of the TRPV1 selective agonist which can be a vanilloid, or in an advantageous embodiment, a capsaicinoid. The analgesic agent is one or more components selected from the group consisting of methyl salicylate, a TRPM8 agonist (e.g., menthol, icilin or eucalyptol), and a TRPV3 agonist (e.g. camphor). In one embodiment, the analgesic agent is greater than 50% by weight of the composition and is capable of solubilizing said TRPV1 selective agonist. In another embodiment, the methyl salicylate is replaced in whole or part by an alcohol such as ethanol.

In an advantageous embodiment the invention discloses a composition comprising:
i) 0.075-30% by weight of a TRPV1 selective agonist, and
ii) 50-95% by weight of an analgesic agent comprising a) a topical salicylate and b) a TRPM8 agonist or a TRPV3 agonist, capable of solubilizing said TRPV1 selective agonist, wherein said composition has an amount of TRPV1 selective agonist sufficient to decrease the density of functional nociceptive nerve fibers when said composition is applied topically, and said composition has an amount of analgesic agent sufficient to eliminate or reduce the burning and/or stinging sensation or erythema created by the topical administration of the TRPV1 selective agonist.

In another embodiment the invention discloses a composition comprising:
0.075-30% by weight of a TRPV1 selective agonist, and
70-95% by weight of an analgesic agent capable of solubilizing said TRPV1 selective agonist, wherein said composition has an amount of TRPV1 selective agonist sufficient to decrease the density of functional nociceptive nerve fibers when said composition is applied topically, and said composition has an amount of analgesic agent sufficient to eliminate or reduce the burning and/or stinging sensation or erythema created by the topical administration of the TRPV1 selective agonist, and wherein said composition does not include turpentine oil.

In a further advantageous embodiment, the composition comprises:
0.075-30% by weight of a capsaicinoid,
30-75% by weight methyl salicylate and/or ethanol,
1-20% by weight menthol, and
1-20% by weight camphor.
Advantageously, 0.2-30%, or 5-20 by weight of a capsaicinoid compound, 30-70% by weight methyl salicylate and/or ethanol, or 40-60% by wt. methyl salicylate and 10-25% by wt. ethanol; 1-20% by weight menthol, more advantageously 10-20%; and 1-20% by weight camphor, more advantageously 5-15%.

In a still further embodiment, the composition comprises a capsaicinoid,
methyl salicylate and/or ethanol, and
phenol.
Advantageously, the composition comprises 0.20-30% by weight of a capsaicinoid compound; 30-75% by weight methyl salicylate and/or ethanol; 1-20% by weight menthol; 1-20% by weight camphor; and 0.5-5% phenol.

In another embodiment (not involving capsaicin or related compound), the composition comprises:
70-95% by weight methyl salicylate and/or an alcohol such as ethyl alcohol,
10-20% by weight menthol,
10-20% by weight camphor, and optionally
0.5-5% phenol.

The invention also relates to methods of making and using compositions for the treatment of pain as well as treating a variety of other medical conditions. Methods of treating pain in a mammal (e.g. human) comprise topically administering the compositions of the invention, and include methods of reducing the density of nociceptor nerve fibers in the dermis and epidermis of a selected region of a mammal, comprising administering the composition of the invention to said region, e.g. where the density of functional nociceptive nerve fibers is decreased by at least 20%, 30%, 40% or 50% after topically administering the composition.

The invention includes methods of treating a capsaicin responsive condition such as pain including neuropathic pain, inflammatory hyperalgia, vulvodynia, interstitial cystitis, rhinitis, burning mouth syndrome, oral mucositis, herpes, dermatitis, pruritis, tinnitus, psoriasis, or headaches, with the compositions of the invention. The invention also includes treating arthritis pain in a mammal, and a method of treating itching in a mammal. Typically, administration is topical application to the affected area.

Also included are methods of formulating a capsaicinoid liquid comprising the capsaicinoid dissolving in methyl salicylate to form a solution, and adding camphor and/or menthol to the solution, and methods of producing a topical formulation of capsaicin comprising mixing capsaicin and methyl salicylate, and adding one or more of menthol, camphor and phenol.

The invention also relates to kits comprising the liquid formulation of the invention and a non occlusive applicator device. In another embodiment the kit further comprises a cleaning solution for removal of residual agonist.

DETAILED DESCRIPTION OF THE INVENTION

Figure 1:
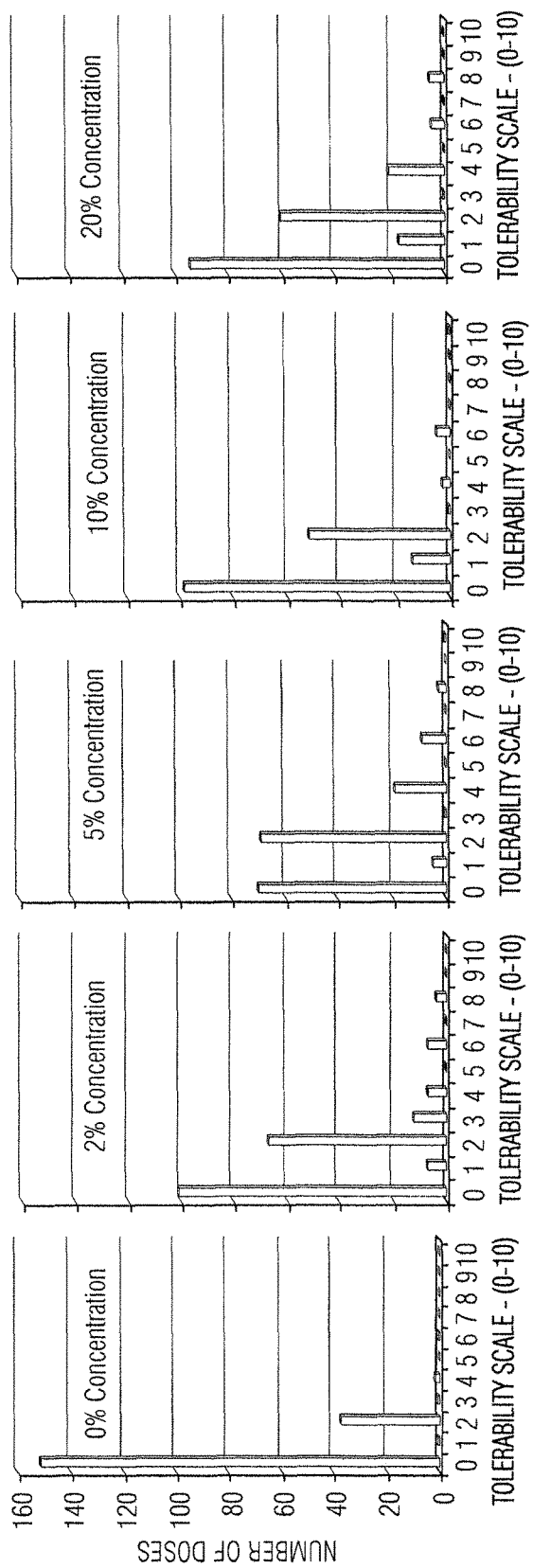
FIG. 1 shows the tolerability of API-CAPS (0%, 2%, 5%, 10% or 20% capsaicin) following once daily, 60 minute exposure, treatment of osteoarthritic knees for 4 consecutive days. Subjects rated tolerability (burning & stinging sensation) at 15, 30, 45, and 60 minutes after API-CAPS application on a 0-10 numeric rating scale (0=no pain; 10=worst pain imaginable) in conjunction with the Wong-Baker Faces Rating Scale as a guide.

The invention relates to compositions, typically liquid solution pharmaceutical formulations, of a TRPV1 selective agonist (i.e. acting as specific agonist for TRPV1 such as does capsaicin) agonist such as capsaicin or a capsaicin derivative/analogue, primarily for the treatment of pain. The compositions include one or more analgesics which reduce or eliminate the burning or stinging pain caused by administration of the TRPV1 selective agonist, thereby making the TRPV1 selective agonist formulation administration tolerable, including in long-term administration. The present application discloses the discovery that a TRPV1 selective agonist containing topical composition is very effective in treating pain in humans, and causes significantly less burning pain at the site of the application, when administered with one or more topical analgesics at high concentration(s) such as methyl salicylate, camphor, menthol and phenol, than the same composition without an analgesic. Unlike conventional formulating where a base vehicle is selected and the actives are added thereto, in the formulations of the subject invention, the actives, the analgesics, are the vehicle or are the primary vehicle. The analgesic components of the formulations of the invention together make up typically greater than 50%, or 60%, 70% or greater than 75% by weight of the formulations.

The present invention provides immediate pain relief from the analgesic agent along with the long lasting pain relief afforded by the TRPV1 selective agonist, e.g. capsaicin, without the same severity of concentration-dependent capsaicin side effects (e.g. stinging and burning) associated with prior art capsaicin formulations. The formulations can provide pain relief for periods of weeks to months dependent upon disease state and severity. Importantly, the formulations of the present invention maintain sensation in the skin onto which the formulation has been topically applied.

The topical formulations, particularly for the treatment of pain, contain higher levels of TRPV1 selective agonists such as capsaicin, than normally used. The subject formulations do not have the discomfort and burning associated with capsaicin formulations of the prior art. The formulations of the TRPV1 selective agonist can include anti-inflammatory, antioxidant and other additives that contribute to pain relief and the therapeutic treatment of pathological conditions such as arthritis pain, osteoarthritis, joint disorders, muscular pain, neuropathic pain, neck and back pain, shingles, cluster headaches and other disease or health-related conditions.

The subject invention relates to pharmaceutical topical compositions for delivery of significant quantities of a TRPV1 selective agonist compound such as capsaicin or related compounds via the skin. The components of the composition other than the TRPV1 selective agonist compound are included to reduce or eliminate the burning sensation associated with administration of the TRPV1 selective agonist compound as well as to enhance skin penetration of said TRPV1 selective agonist compound. The additional components are typically camphor, methyl salicylate and/or alcohol, and menthol, and optionally phenol, which are generally accepted as safe and effective for the temporary relief of minor aches and pains of muscles and joints associated with simple backache, arthritis, strains, bruises and sprains.

It has been discovered that incorporation of a sufficient quantity of these ingredients into the capsaicin preparations forms a mixture for the topical treatment of pain such that the initial burning/stinging pain resulting from capsaicin is eliminated or ameliorated.

It has been demonstrated that the analgesic properties of these ingredients reduce the burning/stinging sensation produced following topical application of a TRPV1 selective agonist compounds such as capsaicin. The compositions of the invention include appreciable quantities of menthol, camphor, and methyl salicylate, and optionally phenol which also enhances the analgesic properties that minimize the burning/stinging sensation produced following topical application capsaicin. Other suitable/compatible analgesic oils such as peppermint oil (which also contains menthol), *eucalyptus* oil, lavender oil and other analgesic oils can be added to the topical mixture. Components can also be added which enhance the penetration of the capsaicin into the viable layers of the skin and into subcutaneous tissues.

Accordingly, the present invention provides topical preparations comprising an amount of a TRPV1 selective agonist such as capsaicin effective in initial and long-term or repeated administration to reduce pain associated with certain cutaneous disorders and neural dysfunctions.

which inhibits the nerve endings that signal pain. The TRPV1 selective agonist component is typically a vanilloid, a capsaicinoid, more specifically capsaicin, nonivamide or other capsaicin analogue, or a mixture thereof.

TRPV1 selective agonist compounds of the subject invention include the natural capsaicinoids (Capsaicin Oleoresin), and synthetic (Nonivamide) forms, as well as derivatives (analogues) of capsaicin. Capsaicin is known by the chemical name N-(4-hydroxy-3-methoxybenzyl)-8-methylnon-trans-6-enamide. Capsaicin is the main capsaicinoid (typically 69%) in chili peppers, followed by dihydrocapsaicin (typically 22%) and norihydrocapsaicin (typically 7%). Nonivamide is found in trace amounts in chili peppers.

| | | | | CAPSAICIN & CAPSAICINOID PROPERTIES | | | |
|---|---|---|---|---|---|---|---|
| Capsaicinoid Name | Abbr. | MW | Natural Relative Amount | Scoville Heat Units | Molecular Formula | | Chemical Structure |
| Capsaicin | C | 305 | 69% | 16 x 10$^6$ | $C_{18}H_{27}NO_3$ | | |
| Dihydro-capsaicin | DHC | 307 | 22% | 15 x 10$^6$ | $C_{18}H_{29}NO_3$ | | |
| Nordihydro-capsaicin | NDHC | 293 | 7% | 9.1 x 10$^6$ | $C_{18}H_{27}NO_3$ | | |
| Homodihydro-capsaicin | HDHC | 321 | 1% | 8.6 x 10$^6$ | $C_{19}H_{31}NO_3$ | | |
| Homo-capsaicin | HC | 319 | 1% | 8.6 x 10$^6$ | $C_{19}H_{29}NO_3$ | | |
| Nonivamide | PAVA | 293 | [1]0.25% | 9.2 x 10$^6$ | $C_{17}H_{27}NO_3$ | | |

[1]Constant et al. J. Nat. Prod. 1996 59, 425-426

Compounds of the Invention

The components of the formulations of the invention are discussed below.

TRPV1 Selective Compounds Including Capsaicinoids, Capsaicin and its Analogues

According to the present invention, the pain relief composition comprises a therapeutically effective amount of a nerve-inhibiting component—a TRPV1 selective agonist, As noted above, capsaicin and several related compounds are called capsaicinoids. Nonivamide, the vanillylamide of n-nonanoic acid (also PAVA) is used as a reference substance for determining the relative pungency of capsaicinoids as well as being used as a food additive to add pungency.

Capsaicin and dihydrocapsaicin together make up 80-90% of the capsaicinoids found in chili peppers. The different capsaicinoid compounds have slight structural variations in the hydrocarbon tail, changing their ability to bind to the nerve receptors and their ability to penetrate layers of receptors on the tongue, mouth, and throat.

Capsaicinoids are very similar in structure, varying only by the length of a long hydrocarbon portion (that is, a portion containing only carbon and hydrogen atoms), and by the presence or absence of one carbon-to-carbon double bond in that hydrocarbon portion (carbon-carbon double bonds).

Nonivamide is present in chili peppers but is commonly manufactured synthetically. It is more heat-stable than capsaicin. Ointments sold to relieve arthritis and muscle pain often contain nonivamide. Application of the ointment on the skin is claimed to result in a warm to burning sensation and pain relief for several hours.

Both the naturally occurring capsaicin and the synthetic capsaicin analogues that differ slightly in their alkyl chain, have similar pharmacological effects.

Capsaicin is practically insoluble in water, but freely soluble in alcohol, methyl salicylate, ether, benzene and chloroform. Capsaicin is a lipophilic white crystalline powder; melting point 60-65 degrees C.

Therapeutically, capsaicin has been used as a topical analgesic. Both the natural and synthetic (forms of capsaicin are available commercially.

Capsaicinoids in addition to capsaicin are applicable to this invention.

Resiniferatoxin (RTX) is a very potent capsaicin analogue. Other TRPV1 selective agonists include anandamide, and NADA. Many additional agonists are disclosed in U.S. Pat. No. 7,943,166 and U.S. Pat. No. 7,632,519, each of which is hereby incorporated by reference in its entirety. Some capsaicin analogues are described in U.S. Pat. No. 5,962,532, hereby incorporated by reference in its entirety.

The formulations of the invention typically include 0.075-30% by weight, 0.2-30%, or 2-20%, 2-10% or 5-15% of capsaicin, or related compounds. When the TRPV1 selective agonist is other than capsaicin, since potency can vary, the amount of agonist in the formulation is that amount which achieves the same results achieved by the weight percent ranges noted herein for capsaicin.

Analgesics and Other Components

The compositions of the subject invention also include an analgesic agent—one or more analgesics. As used herein, an "analgesic agent" is a compound or compounds which, when topically applied, reduces pain or burning sensation without loss of sensation. The analgesics agents of the invention do not include a capsaicinoid and do not include an opioid. Further, the analgesic agents do not include a topical local anesthetic, such as lidocaine (or procaine, amethocaine, cocaine lidocaine (also known as Lignocaine), prilocaine, bupivacaine, levobupivacaine, ropivacaine, mepivacaine, dibucaine) in the TRPV1 specific agonist containing formulations. These caine local anesthetics have not been effective in sufficiently moderating the burning effect of capsaicin when administered concomitantly with capsaicin topically; they have a slower onset of action relative to capsaicin. To reduce the burning sensation, these caine local anesthetics are typically administered in advance of capsaicin attempting to elicit sufficient anesthetic action prior to the burning sensation associated with capsaicin. In one embodiment, the analgesic agent does not include turpentine oil.

Accordingly, it was discovered that a system of analgesic compounds can function to: (1), solubilize appreciable concentrations of the relatively aqueous insoluble capsaicin and related capsaicinoids and TRPV1 selective agonists; (2), rapidly penetrate the skin surface and underlying dermis and epidermis; and (3) reduce or eliminate the burning and stinging sensation and erythema associated with the topical administration of the TRPV1 (e.g. capsaicin), including reducing thermal hyperalgesia (enhanced sensitivity to heat) associated with the topical administration of the TRPV1 selective agonist (e.g. capsaicin) which can occur hours to days after administration of the TRPV1 selective agonist. The subject invention includes the use of specific topical analgesics that have a fast "onset of action" relative to capsaicin (such as methyl salicylate, menthol, camphor, and phenol) to effectively moderate the burning effect of capsaicin when concomitantly administered with capsaicin topically. Onset of action of a compound is linked to its physicochemical properties; some of which are summarized below.

| Ingredients | MW | Oil Soluble | Aqueous Soluble. | Log O/W | MP (° C.) | Onset of Action |
| --- | --- | --- | --- | --- | --- | --- |
| Capsaicin | 305.41 | soluble | insoluble | 3.327 | 62-65 | moderate |
| Methyl Salicylate | 152.15 | Alcohol miscible | sparingly | 2.23 | −9 | fast |
| Ethyl Alcohol | 46.07 | soluble | miscible | −0.18 | −114 | fast |
| Phenol | 94.11 | soluble | soluble | 10 | 43 | fast |
| Menthol | 156.26 | soluble | slightly soluble | 2.66 | 42 | fast |
| Camphor | 152.23 | soluble | Slightly soluble | 2.089 | 176 | fast |
| Lidocaine | 234.34 | soluble | insoluble | 2.359 | 68 | slow |
| Prilocaine | 220.31 | soluble | sparingly | 2.11 | 137 | slow |
| Benzocaine | 165.19 | Soluble | sparingly | 1.95 | 90 | moderate |

The use of these selected topical analgesics with a fast onset of action effectively moderates the burning effect of capsaicin when concomitantly administered topically, but also provides more immediate pain relief relative to capsaicin. In one embodiment of the invention, the topical analgesic agent has a molecular weight of 160 or less. Capsaicin provides more long term/long lasting pain relief relative to these fast onset of action topical analgesics.

The present application includes the discovery that topical TRPV1 selective agonist containing compositions have significantly less burning pain at the site of the application when combined with topical analgesics such as methyl salicylate, camphor, menthol, and phenol (when compared to the same composition without analgesic), and are extremely effective in treating pain in mammals including humans. As used herein, "topical" refers to administration of the composition to a defined area of the body such as a defined area of skin surface or mucous membrane.

The analgesic agent of the invention is one or more agents selected from the group consisting of methyl salicylate and/or alcohol (30-75% by weight), a TRPM8 agonist (e.g. menthol, icilin or eucalyptol), and a TRPV3 agonist (e.g. camphor). The analgesic agent (which can be multiple compounds) is capable of solubilizing the TRPV1 selective agonist. The analgesic components of the formulations of the invention are typically greater than 50% by weight of the formulations.

Topical Salicylates Including Methyl Salicylate

Methyl salicylate can act as an analgesic and anti-inflammatory agent. Some of the plants which produce it are called wintergreens, hence the common name. Trolamine salicylate, the active ingredient in Aspercreme™ is another salicylate which can be used in topical pain compositions. Esters of methyl salicylate have also been made. It has been found that methyl salicylate can be used advantageously as a solvent to dissolve capsaicinoids.

The formulations of the invention typically include 30-70% or 40-60% by weight methyl salicylate.

Menthol

Menthol is an organic compound made synthetically or obtained from peppermint or other mint oils that produces a feeling of cooling. Advantageously, (l)-menthol (natural menthol derived from peppermint oil) is used in the subject invention for analgesic effects. Alternatively, another transient receptor potential subfamily M8 (TRPM8) agonist such as icilin or eucalyptol can be used.

The formulations of the invention include 1-20%, 10-20% by weight menthol.

Camphor

Camphor is readily absorbed through the skin and produces a feeling of cooling similar to that of menthol, and acts as slight local anesthetic. Camphor is a naturally occurring compound. Alternatively, another transient receptor potential vanilloid 3 (TRPV3) agonist such as icilin or eucalyptol can be used.

The formulations of the invention include 1-20%, 10-20%, or 5-15% by weight camphor.

Phenol

Phenol cools and numbs skin on contact, making it an effective topical analgesic ingredient. It also kills germs, and reduces the risk for infection in minor skin irritations. It has been used medically for over 100 years, for these and other applications. Because it can improve the effectiveness of a preparation at relieving itching, phenol is added to formulations meant for the relief of insect bites and stings, sunburn, and other painful and itchy skin conditions.

The formulations of the invention can include 0-4.6%, advantageously 1-3% phenol. Eugenol/clove oil and thymol/thyme oil or an Essential Oil (see Table II or Table below) can be added in addition to, or as alternative to phenol. Below is a listing of natural analgesic ingredients together with some of their properties.

Surfactants and Other Agents that Enhance Skin Penetration

One or more surfactant(s), advantageously non ionic (e.g. polysorbates such as PS80, sorbitan esters (Spans), poloxamers, etc.), can be also be added to the compositions of the invention to enhance the skin penetration of the analgesic and capsaicin compounds. They can ameliorate the initial stinging pain caused by capsaicin (or related compounds) in admixture with the pharmaceutically acceptable carrier ingredients for topical administration. Fatty acid ester non-ionic surfactants which are utilized in pharmaceutical, cosmetics and food stuffs are especially advantageous because of the compatibility with biological tissues.

Other penetrating agents include propylene glycol, αBisabolol, and other oil soluble organic compounds known in the art of topical formulation development which can enhance skin penetration.

Anti-Inflammatory Agents

Apigenin & αBisabolol

An effective amount of an inflammation control component, which reduces or relieves inflammation, swelling, redness, and/or pain in the joints and muscles associated with inflammation, can be added (e.g. apigenin and αbisabolol).

Apigenin offers some of nature's most potent and effective anti-inflammatory and antioxidant properties. It can be included in the formulation to further enhance therapeutic efficacy. Apigenin has a broad range of anti-inflammatory properties and has been cited for the ability to block the production of compounds that cause pain; e.g., the arthritis causing substance cyclooxygenase (COX). The addition of apigenin to a mixture of capsaicin in the constituents of the subject pain relieving formulations can be accomplished using the high temperature surfactant technology where apigenin is first dissolved in PS80 at elevated temperatures to form a concentrate that is then added to the mixture (see US Application US 2011/0311592 A1).

αBisabolol is another potent anti-inflammatory sesquiterpene which is known to also have anesthetic, anti-irritant, anti-inflammatory, anti-fungal and anti-microbial properties.

| NATURAL ANALGESIC INGREDIENTS | FUNCTION | | | | | | | |
|---|---|---|---|---|---|---|---|---|
| | Analgesic | Anesthetic | Antiseptic | Antifungal | Antibacterial | Rubefacient | Anti-Inflammatory | Antipruritic |
| Menthol (Mint Oils) | X | | X | | X | X | X | X |
| Camphor | X | X | X | | X | | X | X |
| Wintergreen Oil (methyl salicylate) | X | | X | | X | X | X | |
| Phenol | X | X | X | X | X | | X | X |
| Eugenol/Clove oil | X | X | X | | X | | X | X |
| Thymol/Thyme Oil | X | X | X | X | X | X | X | X |
| Eucalyptus Oil | X | | X | | X | X | X | X |
| Peppermint Oil | X | | X | | X | X | X | X |
| Lavender Oil | X | | X | | X | | X | X |
| Tea Tree Oil | X | | X | X | X | | X | X |
| Turpentine Oil | X | | X | | X | X | X | X |

Alcohol

In another embodiment of the invention, the methyl salicylate is replaced with, or supplemented with an alcohol such as ethyl alcohol or benzyl alcohol, which like methyl salicylate, can solubilize capsaicinoids as well as menthol and camphor. This results in compositions with lower viscosity and shorter drying times. In one embodiment where the methyl salicylate is replaced with ethanol, glycerol can be added to the composition.

αBisabolol is also demonstrated to enhance the percutaneous absorption of certain molecules. αBisabolol helps transport active ingredients transdermally by enhancing skin penetration. (R. Kadir and B. W. Barry. *Alpha-Bisabolol, a Possible Safe Penetration Enhancer for Dermal and Transdermal Therapeutics. Int. J. Pharm.* 70:87-94 (1991).)

NSAIDs/Diclofenac Sodium

In further embodiments of the invention, a Non-Steroidal Anti-Inflammatory Agent (NSAID) is co-administered with the TRPV-1 selective agonist formulations. The NSAID and the TRPV-1 selective agonist can be administered together as a single composition (where a topical NSAID is used) or administered as separate compositions (where a topical or not topical NSAID is used). The NSAID can be administered before, after or at the same time as the TRPV-1 selective agonist by the same or different routes of administration. For example, the TRPV-1 selective agonist can be administered topically while the NSAID agent can be administered orally, topically or parentally.

NSAIDs useful as adjunctive agents in the formulations of the present invention include aspirin (acetylsalicylic acid), ibuprofen, naproxen, diclofenac, benoxaprofen, ketoprofen, indomethacin etc., and mixtures thereof. As used herein, "NSAID" does not include methyl salicylate.

Combining an NSAID such as a Diclofenac Salt with capsaicin in a topical formulation combines two established pain relieving agents which function via two different mechanisms of action (MOAs); i.e., TRPV1 nerve defunctionalizer and a potent COX-2 inhibitor. Solubility studies were conducted (see below) and formulations were prepared containing the NSAID, diclofenac sodium, together with the TRPV1 selective agonist, capsaicin, utilizing the subject invention.

Odor Reduction Components

Many topically applied analgesic formulations contain a blend of volatile aromatic compounds and essential oils which are used for the temporary relief of minor aches and pains of muscles and joints associated with simple backache, arthritis, sprains, bruises and strains. For example: White Flower Analgesic Balm consists of the active ingredients: Methyl Salicylate (Wintergreen Oil) 40%, Menthol 15%, Camphor 6% and other ingredients; *Eucalyptus* Oil 18%, Peppermint Oil 15%, and Lavender Oil 6%. However, all the components of White Flower Analgesic Balm are known for their distinctive odors such that these combined ingredients do contribute to a strong, penetrating pungent, odor that is objectionable for many users and to many individuals who come in contact with the users. Further, the magnitude of the perceived odor of these volatile aromatic compounds and essential oils often increases within closed spaces such as in automobiles, buses, planes, and poorly ventilated rooms, etc. The teachings of this invention are particularly advantageous in the reduction of the severity of these perceived odors from the aforementioned topical analgesic compounds whose combined concentration often exceeds more than 35% by weight of a formulation.

Inclusion of relatively non-odiferous oils with low ambient vapor pressures such as Aloe Vera, Coconut, Borage and/or Macadamia Nut Oils to formulations containing significant quantities of volatile topical analgesic compounds such as methyl salicylate, camphor and menthol results in a significant reduction in the perception of these strongly penetrating pungent aromatic odors. This effect is particularly useful with formulations having relatively high capsaicin concentrations.

Aloe Vera Oil

Aloe Vera in Aloe Vera Oil is a nutrient rich ingredient used in skin preparations as it contains Vitamin C, E, Beta-Carotene, and B12, minerals such as magnesium, copper, chromium, calcium, iron and potassium, essential amino acids, plant sterols and lignin.

Aloe Vera is rich in anti-inflammatory, emollient, anti-fungal, anti-bacterial and anti-viral properties, making it a potent remedy for many skin ailments. The various enzymes in Aloe Vera reduce the itching, swelling and inflammation that often accompany common skin ailments. Aloe Vera has been used to treat wounds, burns, scalds and even sunburn. The plant extract counters bacterial infection while improving circulation and expediting the healing process. Aloe Vera is useful for cell regeneration.

Coconut Oil

Coconut Oil is useful in the treatment of skin conditions such as eczema, psoriasis, rosacea and various other skin infections; and helps to reduce or eliminate itching and flaking of the skin due to dryness. Coconut Oil contains vitamin E, which is necessary for healthy skin, as well as the medium-chain fatty acids Capric Acid, Caprylic Acid, Caproic Acid and Lauric Acid.

It moisturizes the skin, either alone or in combination with other oils, and is an exceptional base oil for moisturizing creams and oils and aromatherapy blends. Coconut Oil's antioxidant properties can help delay wrinkles and sagging skin related to aging by preventing the formation of free radicals and strengthening the skin's underlying connective tissues, as well as by limiting the damage caused by excessive sun exposure.

Borage Oil

Topical application of borage oil has been shown to be effective in preventing and treating inflammatory conditions and skin disorders, such as eczema and dermatitis, in both animals and humans. Although essential fatty acids are important in diet, they can also play an important role when applied topically to the skin. Borage Oil is the richest known source (24%) of an essential fatty acid called gamma-linolenic acid (GLA). These polyunsaturated essential fatty acids are essential for the structure and flexibility of the cell membranes and also play an important role in the construction of the epidermal lipid barrier. They therefore can help normalize trans-epidermal water loss. Borage oil is extremely high in mucilage and also contains pyrrolizdine alkaloids. The main constituents of the oil are vitamin C, saponins, tannins and minerals. The tannins in the oil have a slight tightening effect on the skin and the oil helps to restore moisture and smoothness to dry skin, soothing irritated and damaged skin. Borage oil also helps provide relief to people who suffer from chronic skin disorders, such as eczema and atopic dermatitis.

Macadamia Nut Oil

This hypoallergenic "oil" contains a high concentration of palmitoleic Acid, 18%, in addition to 60% oleic acid, 2.7% linoleic acid, 3% omega-3 and omega-6. Macadamia Nut Oil indeed is an effective emollient that gives a rich skin feel. The oil has several natural healing properties as well. Many are finding great success using it to help with irritated skin, small wounds, and to reduce the coloration in scars.

The stability of Macadamia Nut Oil makes it an ideal ingredient for an array of cosmetic applications. Macadamia Nut Oil is known to be a protective oil with a respectable and reasonably quick absorption rate. Macadamia Nut Oil acts in a similar way as does the human sebum that naturally protects and lubricates the skin. The oils regenerative properties make it a quality ingredient for products targeting damaged skin.

Compositions of the Invention

The invention relates to a compositions, advantageously a liquid solution, comprising a TRPV1 selective agonist, and an analgesic agent capable of solubilizing said TRPV1 selective agonist, wherein said composition has an amount of TRPV1 selective agonist sufficient to decrease the density of functional nociceptive nerve fibers when said composition is applied topically, and said composition has an amount of analgesic agent sufficient to eliminate or reduce the burning and/or stinging sensation or erythema created by the topical administration of the TRPV1 selective agonist. The liquid solution of the invention is advantageously a non aqueous solution. If ethanol is in the solution, water can be included. Typically, the water is less than 5%, or advantageously less than 2% by wt. In the compositions of the subject invention, inert ingredients (i.e. other than the TRPV1 selective agonist, and the analgesics) typically comprise less than 25%, 10% or 5% by weight, of the composition.

The TRPV1 selective agonists, analgesic agents and excipients suitable for use in the pharmaceutical compositions of the present invention, are those which are pharmaceutically acceptable when applied to human skin, ie having acceptable toxicity at the levels used. All components of the formulations of the invention are USP grade. In a preferred embodiment of the invention, the compositions are manufactured in full compliance with GMP regulations of the U.S. FDA.

In one embodiment, the amount of TRPV1 selective agonist sufficient to decrease the density of functional nociceptive nerve fibers by at least 20%, or at least 50%, after topical application. In another embodiment the composition is 0.20-30% by weight of the TRPV1 selective agonist.

The TRPV1 selective agonist can be a vanilloid, or in an advantageous embodiment, a capsaicinoid such as capsaicin.

The analgesic agent that solubilizes the TRPV1 selective agonist, is one or more agent selected from the group consisting of methyl salicylate (30-70% by weight), a TRPM8 agonist (e.g. menthol, icilin or eucalyptol), and a TRPV3 agonist (e.g. camphor). The analgesic agent is typically greater than 50% by weight of the composition and is capable of solubilizing said TRPV1 selective agonist.

Advantageous components of the compositions of the invention are:
capsaicin or a related compound,
methyl salicylate and/or ethanol,
menthol,
camphor, and optionally
phenol.

When combined with analgesic/desensitizing ingredients, the amount of capsaicin (e.g. trans-capsaicin) in the topical preparation can be from 0.075-30 wt. %, 0.2 wt. % to 30 wt. %, between 1 wt. % and 20 wt. %, e.g. 1 wt. %, 5 wt. %, 10 wt. %, and 20 wt. %.

The amount of analgesic ingredients to achieve the above effect is greater than 50 wt. %, or in the range of 60 wt. % to 95 wt. % of the preparation.

Advantageous formulations of the invention include (by weight):
methyl salicylate and/or ethanol ~30-75 wt. %, advantageously 40-60 wt. %
menthol, ~1-20 wt. %, advantageously 10-20 wt. %
camphor ~1-20 wt. %, advantageously 5-15 wt. %, and optionally
phenol ~0-4.6 wt. %, advantageously 0.5-2 wt. %.

Advantageous embodiment of the invention without a TRPV1 selective agonist includes: a composition comprising:
30-75% by weight methyl salicylate and/or ethanol,
1-20% by weight menthol,
1-20% by weight camphor, and
optionally phenol,
wherein the percentage by weight of the methyl salicylate, menthol, and camphor is greater than 50% of the composition;

In another embodiment, the invention includes
a composition comprising:
a capsaicinoid,
methyl salicylate and/or ethyl alcohol, and
phenol,
wherein the percentage by weight of the methyl salicylate and phenol is greater than 50% of the composition. More specifically in this embodiment the composition can comprise:
0.075-30% by weight of a capsaicinoid compound,
30-75% by weight methyl salicylate and/or ethyl alcohol, and
0.5-5% phenol.

Table III, IIIA, and IIIB contain a listing of the compositions of several prepared Nonivamide and Capsaicin formulations.

TABLE III

INGREDIENTS OF PREPARED NONIVAMIDE FORMULATIONS

| INGREDIENTS | Form 1 Wt % | Form 2 Wt % | Form 3 Wt % | Form 4 Wt % | Form 5 Wt % | [16]Form 6 Wt % | [16]Form 7 Wt % | Form 8 Wt % | Form 9 Wt % | Form 10 Wt % | Form 11 Wt % |
|---|---|---|---|---|---|---|---|---|---|---|---|
| [1]NONIVAMIDE | 0.2 | 1.8 | 4 | 1.8 | 1.8 | 1.8 | 1.8 | 1.8 | 1.8 | 1.8 | 0.25 |
| [2]METHYL SALICYLATE | 20 | 35 | 45 | 35 | 49.2 | 55 | 55 | 55 | 55 | 55 | 45 |
| [3]MENTHOL | 6 | 13 | 15 | 13 | 15 | 15 | 0 | 15 | 0 | 0 | 15 |
| [4]CAMPHOR | 3 | 6 | 8 | 9 | 11 | 0 | 10 | 0 | 10 | 0 | 10 |
| [5]PHENOL | 0 | 0 | 0 | 1.5 | 2 | 0 | 0 | 0 | 0 | 0 | 2 |
| [6]αBISABOLOL NATURAL | 0 | 0 | 0 | 1 | 1 | 0 | 0 | 0 | 0 | 0 | 0 |
| [7]HYDROCORTISONE | 1 | 1 | 1 | 0 | 0 | 0 | 0 | 0 | 0 | 0 | 0 |
| [8]POLYSORBATE 80 | 9.25 | 9.25 | 9.25 | 9.25 | 9.25 | 0 | 0 | 0 | 0 | 0 | 0 |
| [9]APIGENIN | 0.75 | 0.75 | 0.75 | 0.75 | 0.75 | 0 | 0 | 0 | 0 | 0 | 0 |
| [10]ETHYL ALCOHOL | 0 | 0 | 0 | 0 | 10 | 20 | 20 | 20 | 20 | 20 | 10 |

TABLE III-continued

INGREDIENTS OF PREPARED NONIVAMIDE FORMULATIONS

| | | | | | | | | | | | |
|---|---|---|---|---|---|---|---|---|---|---|---|
| (11)GLYCEROL | 0 | 0 | 0 | 0 | 0 | 8.2 | 9 | 0 | 00 | 0 | 0 |
| (12)PROPYLENE GLYCOL | 0 | 0 | 0 | 0 | 0 | 0 | 4.2 | 0 | 0 | 0 | 0 |
| Balance Including: Aloe Vera, Coconut & Macadamia Nut Oils | (13)59.8 | (13)33.2 | (13)17.0 | (13)28.7 | 0 | 0 | 0 | (14)8.2 | (14)13.2 | (14)23.2 | (14)17.75 |
| TOTAL | 100 | 100 | 100 | 100 | 100 | 100 | 100 | 100 | 100 | 100 | 100 |

| INGREDIENTS | Form 12 Wt % | Form 13 Wt % | Form 14 Wt % | Form 15 Wt % | Form 16 Wt % |
|---|---|---|---|---|---|
| (1)NONIVAMIDE | 0.25 | 5 | 10 | 15 | 1.8 |
| (2)METHYL SALICYLATE | 45 | 50 | 50 | 50 | 50 |
| (3)MENTHOL | 15 | 15 | 15 | 15 | 15 |
| (4)CAMPHOR | 10 | 11 | 11 | 10.5 | 11 |
| (5)PHENOL | 2 | 2 | 2 | 1.5 | 2 |
| (6)αBISABOLOL NATURAL | 0 | 1 | 1 | 1 | 0 |
| (7)HYDROCORTISONE | 0 | 0 | 0 | 0 | 0 |
| (8)POLYSORBATE 80 | 9.25 | 9.25 | 9.25 | 7.4 | 0 |
| (9)APIGENIN | 0.75 | 0.75 | 0.75 | 0.60 | 0 |
| (10)ETHYL ALCOHOL | 10 | 0 | 0 | 0 | 0 |
| (11)GLYCEROL | 0 | 0 | 0 | 0 | 0 |
| (12)PROPYLENE GLYCOL | 0 | 0 | 0 | 0 | 0 |
| Balance Including: Aloe Vera, Coconut & Macadamia Nut Oils | (14)7.75 | (15)6 | (15)1 | 0 | (15)20.2 |
| TOTAL | 100 | 100 | 100 | 100 | 100 |

NOTE:
(1)Nonivamide, Aversion Technologies Inc., CAS # 2444-46-4
(2)Methyl Salicylate, Spectrum Chemical, NF, CAS # 119-36-8
(3)L-Menthol, Crystal, Spectrum Chemical, USP, CAS # 2216-51-5
(4)Camphor, Synthetic, Spectrum Chemical, USP, CAS # 76-22-2
(5)Phenol, Liquefied (Carbolic Acid), USP, Spectrum Chemical, CAS # 108-95-2
(6)Alpha Bisabolol Natural (96%) from Alpha Aesar, CAS # 515-69-5
(7)Hydrocortisone, USP, Spectrum CAS 50-23-7
(8)Polysorbate 80, Super refined, Croda Inc., CAS # 9005-65-6
(9)Apigenin 98%,? Skyherb Technologies Co., Ltd, Lot # 0000418019
(10)Ethyl Alcohol, Graves Grain Alcohol, 190 Proof
(11)Glycerin, Lotioncrafters, USP, CAS # 56-81-5
(12)Propylene Glycol,
(13)Aloe Vera Oil obtained from Spectrum Chemical, Product # A1612, CAS # 85507-69
(14)Coconut Oil, Nature's Way EfaGold Coconut Oil, Pure Extra Virgin
(15)Macadamia Nut Oil, CAS # 128497-20-1, Lotioncrafters Lot # 1506-3187
(16)The shaded highlighted columns, Form 6 & 7, experienced phase separation

TABLE IIIA

INGREDIENTS OF PREPARED CAPSAICIN FORMULATIONS

| INGREDIENTS | Form 1A Wt % | Form 2A Wt % | Form 3A Wt % | Form 4A Wt % | Form 5A Wt % | Form 6A Wt % | Form 7A Wt % | Form 8A Wt % | Form 9A Wt % | Form 10A Wt % |
|---|---|---|---|---|---|---|---|---|---|---|
| (1) CAPSAICIN, NATURAL | 0.25 | 1.8 | 0 | 0 | 0 | 0 | 0 | 0 | 0 | 0 |
| (2) TRANS-CAPSAICIN | 0 | 0 | 0.25 | 0.25 | 2.0 | 2.0 | 5.0 | 10.0 | 15.0 | 20 |
| (3) METHYL SALICYLATE | 0 | 0 | 50 | 50 | 50 | 50 | 50 | 50 | 50 | 50 |
| (4) MENTHOL | 0 | 0 | 15 | 15 | 15 | 15 | 15 | 15 | 15 | 15 |
| (5) CAMPHOR | 0 | 0 | 11 | 11 | 11 | 11 | 11 | 11 | 11 | 11 |
| (6) PHENOL | 0 | 0 | 1.5 | 1.5 | 1.5 | 1.5 | 1.5 | 1.5 | 1.5 | 1.5 |
| (7) POLYSORBATE 80 | 9.25 | 9.25 | 0 | 9.25 | 0 | 9.25 | 0 | 0 | 0 | 0 |

TABLE IIIA-continued

INGREDIENTS OF PREPARED CAPSAICIN FORMULATIONS

| INGREDIENTS | Form 1A Wt % | Form 2A Wt % | Form 3A Wt % | Form 4A Wt % | Form 5A Wt % | Form 6A Wt % | Form 7A Wt % | Form 8A Wt % | Form 9A Wt % | Form 10A Wt % |
|---|---|---|---|---|---|---|---|---|---|---|
| (8) APIGENIN | 0.75 | 0.75 | 0 | 0.75 | 0 | 0.75 | 0 | 0 | 0 | 0 |
| (9) WHITE FLOWER ANALGESIC BALM | 89.75 | 88.2 | 0 | 0 | 0 | 0 | 0 | 0 | 0 | 0 |
| (10) MACADAMEA NUT OIL | 0 | 0 | 22.25 | 12.25 | 20.50 | 10.50 | 17.50 | 12.50 | 7.50 | 2.50 |
| TOTAL | 100 | 100 | 100 | 100 | 100 | 100 | 100 | 100 | 100 | 100 |

NOTE:
(1) Natural Capsaicin, Sigma Aldrich, Product # 360376, CAS # 404-86-4, 65% Capsaicin & 35% Dihydrocapsaicin
(2) Trans-Capsaicin, Aversion Technologies Inc., 95.7% Trans-Capsaicin, Balance Cis-Capsaicin, Batch # 30111007N, USP 30
(3) Methyl Salicylate, Spectrum Chemical, (NF, CAS # 119-36-8)
(4) L-Menthol, Crystal, Spectrum Chemical, USP, CAS # 2216-51-5
(5) Camphor, Synthetic, Spectrum Chemical, USP, CAS # 76-22-2
(6) Phenol, Liquefied, USP, Spectrum Chemical, CAS # 108-95-2
(7) Polysorbate 80, Super refined, Croda Inc., CAS # 9005-65-6
(8) Apigenin 98+%, Skyherb Technologies Co., Ltd, Lot # 0000418019
(9) White Flower Analgesic Balm, Contains 40% Methyl Salicylate, 15% Menthol, 6% Camphor, 18% Eucalyptus Oil, 15% Peppermint Oil, & 6% Lavender Oil
(10) Macadamia Nut Oil, Lotioncrafters Lot # 1506-3187

TABLE IIIB

INGREDIENTS OF PREPARED ESSENTIAL OIL-FREE CAPSAICIN FORMULATIONS

| INGREDIENTS | Form 1B Wt % | Form 2B Wt % | Form 3B Wt % | (9)Form 4B Wt % | (9)Form 5B Wt % | Form 6B Wt % | Form 7B Wt % | Form 8B Wt % | Form 9B Wt % | Form 10B Wt % | Form 11B Wt % | Form 12B Wt % |
|---|---|---|---|---|---|---|---|---|---|---|---|---|
| (2)TRANS-CAPSAICIN | 0 | 0.25 | 2.0 | 5.0 | 0 | 5.0 | 0 | 0.25 | 2.0 | 5.0 | 10 | 0 |
| (2)ETHYL ALCOHOL | 50 | 50 | 50 | 50 | 0 | 0 | 22.5 | 22.25 | 20.5 | 17.5 | 12.5 | 0 |
| (3)METHYL SALICYLATE | 0 | 0 | 0 | 0 | 50 | 50 | 50 | 50 | 50 | 50 | 50 | 50 |
| (4)MENTHOL | 15 | 15 | 15 | 15 | 15 | 15 | 15 | 15 | 15 | 15 | 15 | 15 |
| (5)CAMPHOR | 11 | 11 | 11 | 11 | 11 | 11 | 11 | 11 | 11 | 11 | 11 | 11 |
| (8)PHENOL | 1.5 | 1.5 | 1.5 | 1.5 | 1.5 | 1.5 | 1.5 | 1.5 | 1.5 | 1.5 | 1.5 | 1.5 |
| (7)GLYCERIN, USP | 22.5 | 22.25 | 20.5 | 17.5 | 22.5 | 17.5 | 0 | 0 | 0 | 0 | 0 | 0 |
| (8)MINERAL OIL, USP | 0 | 0 | 0 | 0 | 0 | 0 | 0 | 0 | 0 | 0 | 0 | 22.5 |
| TOTAL | 100 | 100 | 100 | 100 | 100 | 100 | 100 | 100 | 100 | 100 | 100 | 100 |

NOTE:
(1)Trans-Capsaicin, Aversion Technologies Inc., 95.7% Trans-Capsaicin, Balance Cis-Capsaicin, USP 30
(2)Ethyl Alcohol, Graves Grain Alcohol, 190 Proof
(3)Methyl Salicylate, Spectrum Chemical, NF, CAS # 119-36-8
(4)L-Menthol, Crystal, Spectrum Chemical, USP, CAS # 2216-51-5
(5)Camphor, Synthetic, Spectrum Chemical, USP, CAS # 76-22-2
(6)Phenol, Liquefied (Carbolic Acid), USP, Spectrum Chemical, CA 108-95-2
(7)Glycerin, Lotioncrafters, USP, CAS # 56-81-5
(8)Mineral Oil, USP Grade, CVS
(9)The shaded highlighted columns, Form 5B & 6B, experienced phase separation In other embodiments, the formulation can be a spray or gel. Topical compositions of the present invention can be formulated as an emulsion using water and a surfactant or emulsifying system, along with the liquid formulations discussed above.

Methods of Making the Formulations

Capsaicin, nonivamide, camphor and menthol are solids at room temperatures with melting points of 60-62° C., 54° C., 175-177° C., and 42-45° C., respectively. Significantly, methyl salicylate functions as the prime solubilizing agent for the relatively aqueous insoluble solid capsaicin, camphor and menthol ingredients. Methyl salicylate is a liquid at room temperature (with a melting point of −9° C.) and with concentration levels up to 75 wt. %, is the formulation's most concentrated ingredient. (As noted in Table III, the analgesic agent concentration exceeded >50% for several of the formulations.)

A series of solubility experiments verified that the solubility levels of nonivamide in methyl salicylate exceeded 25 wt. %. The addition of nonivamide powder to the 30 wt. % nonivamide/methyl salicylate solution at ambient temperature and also cooling the 30 wt. % nonivamide/methyl salicylate solution to −10° C. for 10 hours did not result in the precipitation of nonivamide thereby indicating the utility of the methyl salicylate as a solvent. Further, there was no evidence of any precipitation of nonivamide from the concentrated 30 wt. % nonivamide solution after 2 weeks of storage at 5° C. Similar results were obtained with capsaicin.

Consequently, methyl salicylate functions as a primary component in a mixture of compounds to: (1), solubilize appreciable concentrations of the relatively aqueous insoluble capsaicin, related capsaicinoids and other solid ingredients including menthol and camphor; (2), penetrate the skin surface and underlying dermis and epidermis; and (3), reduce or eliminate the burning and stinging (B&S) sensation associated with the topical administration of a capsaicinoid.

Initial capsaicin formulations with concentrations ranging from 0.25-10.0 wt. % were prepared with White Flower Analgesic Balm and apigenin/Polysorbate 80 concentrate as detailed in Example 1 below. White Flower Analgesic Balm consists of the ingredients: Methyl Salicylate (Wintergreen Oil) 40%, Menthol 15%, Camphor 6% and *Eucalyptus* Oil 18%, Peppermint Oil 15%, and Lavender Oil 6%.

Example 1 describes the preparation Formulation 2A (Table IIIA) of a 1.8 wt. % Capsaicin, 0.75 wt. % Apigenin & White Flower Analgesic Balm Formulation.

Example 2 describes the preparation of Formulation 9 (Table III) containing a Nonivamide concentration of 1.8 wt. %.

Example 3 describes the preparation of Formulation 4 (Table III) containing a Nonivamide concentration of 1.8 wt. %.

Example 4 describes the preparation of Formulation 11 (Table III) containing a Nonivamide concentration of 0.25 wt. %.

Example 5 describes the preparation of Formulation 7A (Table IIIA) containing a Trans-Capsaicin concentration of 5 wt. %.

Example 6 describes the preparation of Formulation 6A (Table IIIA) containing a Trans-Capsaicin concentration of 2.0 wt. %.

Example 7 describes the preparation of Formulation 3B (Table IIIB), an alcohol based formulation, containing a Trans-Capsaicin concentration of 2.0 wt. %.

Example 8 describes the preparation of Formulation 9B (Table IIIB) containing ethyl alcohol and a Trans-Capsaicin concentration of 2.0 wt. %.

Example 9 describes methods of using the formulations.

Example 10 describes human skin tests of nonivamide and trans-capsaicin formulations.

Example 11 describes treatment of shoulder pain with trans-capsaicin 0.25% and 2.0% formulations.

Example 12 describes API-CAPS-001: a randomized, single-blind, multiple dose study of the safety and tolerability of API-CAPS in subjects with osteoarthritis of the knee.

Example 13 describes API-CAPS-004: 0.25% API-CAPS topical treatment for osteoarthritis pain in hands and knees of adult patients.

Example 14 describes API-CAPS-005: multiple dose case studies of treatment with API-CAPS for pain from osteoarthritis in the elderly.

Example 15 describes components elimination comparison.

Example 16 describes API-CAPS-002, cohort 1: 0.25% API-CAPS (0.25% w/w trans-capsaicin, USP) & capzasin HP arthritis pain relief analgesic cream (0.1% capsaicin).

Example 17 describes diclofenac solubility studies.

Methods of Using the Formulations

Pain

The compositions of the present invention discussed above can be used for treating various conditions associated with pain by attenuating pain at a specific site. The components of the formulations are typically administered concomitantly. Examples of conditions to be treated include, but are not limited to, nociceptive pain (pain transmitted across intact neuronal pathways), neuropathic pain (pain caused by damage to neural structures), pain from nerve injury (neuromas and neuromas in continuity), pain from neuralgia (pain originating from disease and/or inflammation of nerves), pain from myalgias (pain originating from disease and/or inflammation of muscle), pain associated with painful trigger points, pain from tumors in soft tissues, pain associated with neurotransmitter-dysregulation syndromes (disruptions in quantity/quality of neurotransmitter molecules associated with signal transmission in normal nerves) and pain associated with orthopedic disorders such as conditions of the foot, knee, hip, spine, shoulders, elbow, hand, head and neck.

Neuropathic pain generally involves abnormalities in the nerve itself, such as degeneration of the axon or sheath. For example, in certain neuropathies the cells of the myelin sheath and/or Schwann cells may be dysfunctional, degenerative and may die, while the axon remains unaffected. Alternatively, in certain neuropathies just the axon is disturbed, and in certain neuropathies the axons and cells of the myelin sheath and/or Schwann cells are involved. Neuropathies may also be distinguished by the process by which they occur and their location (e.g. arising in the spinal cord and extending outward or vice versa). Direct injury to the nerves as well as many systemic diseases can produce this condition including AIDS/HIV, Herpes Zoster, syphilis, diabetes, and various autoimmune diseases. Neuropathic pain is often described as burning, or shooting type of pain, or tingling or itching pain and may be unrelenting in its intensity and even more debilitating than the initial injury or the disease process that induced it.

The receptors involved in pain detection are aptly enough referred to as nociceptor-receptors for noxious stimuli. These nociceptors are free nerve endings that terminate just below the skin as to detect cutaneous pain. Nociceptors are also located in tendons and joints, for detection of somatic pain and in body organs to detect visceral pain. Pain receptors are very numerous in the skin, hence pain detection here is well defined and the source of pain can be easily localized. In tendons, joints, and body organs the pain receptors are fewer. The source of pain therefore is not readily localized. Apparently, the number of nociceptors also influences the duration of the pain felt. Cutaneous pain typically is of short duration, but may be reactivated upon new impacts, while somatic and visceral pain is of longer duration. It is important to note that almost all body tissue is equipped with nociceptors. As explained above, this is an important fact, as pain has primary warning functions. Nociceptive pain preferably includes, but is not limited to post-operative pain, cluster headaches, dental pain, surgical pain, pain resulting from severe burns, postpartum pain, angina, genitor-urinary tract pain, pain associated with sports injuries (tendonitis, bursitis, etc.) and pain associated with joint degeneration and cystitis.

Topical preparations of the compositions of the present invention find use as a topical therapy for a variety of skin disorders that involve pain and itching, such as postherpetic neuralgia, diabetic neuropathy, psoriasis, cluster headache, postmastectomy pain syndrome, rhinopathy, oral mucositis, cutaneous allergy, detrusor hyperreflexia, loin pain/hematuria syndrome, neck pain, amputation stump pain, reflex sympathetic dystrophy, pain due to skin tumor and arthritis, including rheumatoid arthritis, osteoarthritis, diabetic neuropathy, psoriasis, pruritus (itching), cluster, headache, post-surgical pain, oral pain, and pain caused by injury, amongst others. The formulations can be used to relieve aches and pains of muscles and joints.

As used herein, a "therapeutically effective amount" refers to the quantity or dose of an agent to produce a clinically desired result such as a biological or chemical response, or reduction or elimination of a symptom of a disease or condition, e.g. reduction in or elimination of pain.

Administration

Topical

The composition of the present invention can be used topically by rubbing over an area to be treated. A typical method of use is to rub the formulation over the entire area, until the formulation disappears, and use about 1 to 3 or 4 times daily. Additionally, the amount of formulation used can be gradually increased with each successive application. Topical administration can continue for 1-7 days, weeks, or months.

In certain embodiments, the administration of a TRPV1 selective agonist, such as capsaicin, formulations at the discrete site provides pain attenuation or pain relief for at least about 48 hours to about 16 weeks.

Several methods are available for the dispensing of the capsaicin formulations on the skin's surface. TRPV1 selective agonist containing formulation can be applied by physical means including applicator pads, swabs, or other devices intended to apply the formulations in a thin film such as roller bottles, felt tip or sponge tip applicators.

Roller Bottles

For liquids formulations, dispensers can include bottles with a constriction to facilitate fluid droplet application to the skin. Especially advantageous for capsaicin containing liquid formulations are tubes and/or bottles with a sponge or a 'roll on' applicator.

Roll on bottles (also referred to as roller bottles) are especially advantageous. The roll on bottle greatly simplifies the dispensing of the fluid on the skin's surface. No finger rubbing or Q-tip application is required. The movement of the roller ball on the skin massages the fluid into the skin.

The roll on bottle has a plastic, glass or metal roll on ball and glass or suitable plastic housing. As the ball rolls it picks up the solution and applies it to the skin's surface. The caps of roll on bottles may contain a special ring on the inner side. This ring presses on the ball when the cap is tightly shut. The pressure on the ball prevents leakage of the product.

After filling the bottles, the roll on housing and ball are fitted into the mouth of the bottle. The roll on housing and ball is fitted by pushing the housing into the mouth of the bottle.

Precise control over where the formulation is applied important. The roller-ball provides a more precise control where the formulation is to be applied, to avoid contact with eyes, contact lenses, tender skin, clothing, etc. The "roll on bottle" minimizes the likelihood of causing lip and/or eye burning since finger application is not required to spread a film of the capsaicin solution on the body.

The roll on bottle configuration allows the TRPV1 selective agonist compositions to be applied as a thin homogeneous film. Generally, the application of a thin film formulation is rapidly absorbed into the skin's surface following application. In several embodiments, substantially complete disappearance of the film is complete within 15 minutes following application, and more usually within 10 minutes, or with some embodiments, even less than 5 minutes after application.

Intranasal

When used intranasally, capsaicin irritates the nasonasal area. However, the area becomes desensitized to the irritation after repeated use. Nerve endings responsible for rhinorrhea, sneezing, and congestion become desensitized when capsaicin is applied to the nasal mucosa. Capsaicin use has been targeted at patients presenting congestion, rhinorrhea, sneezing, or a combination of these symptoms. Clinical studies revealed a 60% reduction in nasal airway resistance. In most patients, effectiveness continued for more than 4 months.

Kits

The invention also includes kits comprising a liquid TRPV1 selective agonist composition, and a non-occlusive applicator device. The kit can also include a cleaning solution for removal of residual TRPV1 selective agonist such as polyethylene glycol.

The present invention will be further understood after careful consideration is given to the following non-limiting examples thereof.

EXAMPLES

Example 1

Preparation of 100 Grams of the 1.8 wt. % Capsaicin, 0.75 wt. % Apigenin & White Flower Analgesic Balm Formulation Form 2A, Table IIIA Step I—Preparation of the Apigenin/Polysorbate 80 (PS80) Concentrate Ingredients Include:

9.25 grams of Super Refined PS80, CRODA, Inc. CAS #9005-65-6

0.75 grams of Apigenin powder, Skyherbs Technologies Co., Lot #0000418019

Procedure:

1. Add 9.25 grams of the Super Refined PS80 to a 50 cc "Pyrex" beaker.
2. Add 0.75 grams of Apigenin powder to the PS80.
3. Heat the PS80/Apigenin mixture to a temperature slightly in excess of ~275° C. At about 200° C., it will be observed that the mixture will take on a light brown/reddish color which will darken when the Apigenin is completely solubilized at ~275° C.
4. The Apigenin/PS80 solution is set aside and allowed to cool to <100° C.

Step II—the Preparation of a Liquid Solution of Selected Ingredients

Ingredients:

88.2 grams of While Flower Analgesic Balm 1.8 grams of Capsaicin, Natural, Sigma Aldrich, CAS #404-86-4

Procedure:

1. Obtain the "tare weight" of a ~200 cc beaker & add 88.2 grams of White Flower Analgesic Balm.
2. Add 1.8 grams of Capsaicin, Natural to the mixture from Step 1. Heat the mixture to about 40 to 50° C. to hasten the dissolving of the Capsaicin powder. (Note: Adhere to safety precautions in the handling of the powder.
3. Heat the above mixture to ~40° C. to 50° C. while stirring to hasten the solution of the capsaicin.
4. Allow the solution mixture from Step 3 to cool to room temperature.

Step III—the Combining of the Step I & II Solutions

Mixtures & Subsequent Centrifuging

Ingredients Include:
The solution mixture from STEP I
The solution mixture from STEP II.
Procedure:
1. The Apigenin/PS80 solution from STEP I is added to the solution mixture from STEP II and the combined mixture is thoroughly stirred.
2. The solution mixture from Step 1 is now ready to be centrifuged for 30 minutes in a MicroCentrifuge with a fixed speed of 3,100 RPM for 30 minutes (A Thermo Fischer Model 004480 F Microcentrifuge with slots for 6 15 ml centrifuge tubes). The solution mixture from Step 1 is evenly divided amongst the 15 ml centrifuge tubes which are placed within the centrifuge. The centrifuge's timer is then set for 30 minutes which then activates the spinning process.
3. At the conclusion of the centrifugation process from Step 2, the supernatant liquid from each of the centrifuge tubes is decanted into a 200 ml Pyrex beaker.
4. The mixture from Step 3 is now ready for subsequent packaging.

Example 2

Preparation of 100 Grams of the 1.8% Nonivamide/Apigenin Formulation

Form 9, Table III

Step I—the Preparation of a Liquid Solution of Selected Ingredients & Capsaicin Ingredients:
55 grams of NF grade Methyl Salicylate, Spectrum Chemical, CAS #119-36-8
10 grams of USP grade Camphor, Spectrum Chemical, CAS #76-22-2
1.8 grams of Nonivamide obtained from Aversion Technologies CO.; Bowie, Md., CAS #2444-46-4
20 grams of Ethyl Alcohol, Graves grain alcohol, 190 Proof
Procedure:
1. Obtain the "tare weight" of a ~200 cc beaker & add 55 grams of NF grade Methyl Salicylate.
2. Add 10 grams of USP grade Camphor flakes to the mixture of Step 1. Heat the mixture to ~40° C. to hasten the dissolving of the Camphor flakes while stirring.
3. Add 1.8 grams of Nonivamide to the mixture from Step 2. Heat the mixture to ~40 to 50° C. to hasten the dissolving of the Nonivamide powder. (Note: Adhere to safety precautions in the handling of the powder.)
4. Allow the solution mixture from Step 3 to cool to room temperature and add 20 grams of Ethyl Alcohol.

Step II—the Addition of Other Ingredients to the Liquid Solution from Step I Ingredients Include:
The solution mixture from STEP I
13.2 grams of Coconut Oil, Nature's Way EfaGold Coconut Oil, Pure Extra Virgin Procedure:
1. Add 13.2 grams of the Aloe Vera Oil to the mixture from Step I and thoroughly stir the resulting solution mixture. The mixture is now ready for subsequent packaging.

Example 3

Preparation of 100 Grams of the 1.8% Nonivamide/Apigenin Formulation Form, 4 Table III

Step I—PREPARATION OF THE APIGENIN/POLYSORBATE 80 (PS80) Concentrate

Ingredients Include:
9.25 grams of Super Refined PS80, CRODA, Inc. CAS #9005-65-6
0.75 grams of Apigenin powder, Skyherbs Technologies Co., Lot #0000418019
Procedure:
1. Add 9.25 grams of the Super Refined PS80 to a 50 cc "Pyrex" beaker.
2. Add 0.75 grams of Apigenin powder to the PS80.
3. Heat the PS80/Apigenin mixture to a temperature slightly in excess of ~275° C. At about 200° C., the it will be observed that the mixture will take on a light brown/reddish color which will darken when the Apigenin is completely solubilized at ~275° C.
4. The Apigenin/PS80 solution is set aside and allowed to cool to <100° C.

Step II—the Preparation of the Selected Ingredients & Nonivamide Mixture

Ingredients:
35 grams of NF grade Methyl Salicylate, Spectrum Chemical, CAS #119-36-8
13 grams of USP grade Menthol, Spectrum Chemical, CAS #2216-51-5
9 grams of USP grade Camphor, Spectrum Chemical, CAS #76-22-2
1.8 grams of Nonivamide obtained from Aversion Technologies Co.; Bowie, Md., CAS #2444-46-4
Procedure:
1. Obtain the "tare weight" of a ~200 cc beaker & add 35 grams of NF grade Methyl Salicylate
2. Add 13 grams of USP grade menthol crystals to the Methyl Salicylate (Step 1).
3. Add 9 grams of USP grade Camphor flakes to the mixture of Step 2. Heat the mixture to ~40° C. to hasten the dissolving of the menthol & Camphor while stirring.
4. Add 1.8 grams of Nonivamide to the mixture from Step 3. Heat the mixture to 40 to 50° C. to hasten the dissolving of the Nonivamide powder. (Note: Adhere to safety precautions in the handling of the powder.)

Step III—the Combining of the Step I & II Solutions Mixtures & Subsequent Centrifuging Ingredients Include:
The solution mixture from STEP I
The solution mixture from STEP II.
Procedure:
1. The Apigenin/PS80 solution from STEP I is added to the solution mixture from STEP II and the combined mixture is thoroughly stirred.
2. The solution mixture from Step 1 is now ready to be centrifuged for 30 minutes in a MicroCentrifuge with a fixed speed of 3,100 RPM for 30 minutes (A Thermo Fischer Model 004480 F Microcentrifuge with slots for 6 15 ml centrifuge tubes). The solution mixture from Step 1 is evenly divided amongst the 15 ml centrifuge tubes which are placed within the centrifuge. The centrifuge's timer is then set for 30 minutes which then activates the spinning process.
3. At the conclusion of the centrifugation process from Step 2, the supernatant liquid from each of the centrifuge tubes is decanted into a 200 ml Pyrex beaker.

Step IV—the Addition of Other Ingredients to the Supernatant Liquid from Step III Ingredients Include:
The solution mixture from STEP III
1 gram of Apha Bisabolol Natural, Aloha Aesar, CAS #515-69-5
1.5 grams of Liquefied Phenol USP grade, Spectrum Chemical, CAS #108-95-2
28.7 grams of Aloe Vera Oil, Spectrum Chemical, Product # A1612, CAS #85507-69
Procedure:
1. Add 1 gram of Alpha Bisabolol Natural to the solution mixture from STEP III.
2. Add 1.5 grams of Liquefied Phenol USP grade to the solution mixture from Step 1 and stir the resulting solution mixture.
3. Add 28.7 grams of Aloe Vera Oil to the mixture from Step 2 and thoroughly stir the resulting solution mixture.
4. The mixture from Step 3 is now ready for subsequent packaging.

Example 4

Preparation of 100 Grams of the 0.25% Nonivamide/Apigenin Formulation

Form 11, Table III

Step I—the Preparation of a Liquid Solution of Selected Ingredients & Capsaicin

Ingredients:
45 grams of NF grade Methyl Salicylate, Spectrum Chemical, CAS #119-36-8
15 grams of USP grade Menthol, Spectrum Chemical, CAS #2216-51-5
10 grams of USP grade Camphor, Spectrum Chemical, CAS #76-22-2
2 grams of Liquefied Phenol U.S.P., Spectrum Chemical, CAS #108-95-2
1.8 grams of Nonivamide, Aversion Technologies Co.; Bowie, Md., CAS #2444-46-4
10 grams of Ethyl Alcohol, Graves grain alcohol, 190 Proof
Procedure:
1. Obtain the "tare weight" of a ~200 cc beaker & add 45 grams of NF Methyl Salicylate.
2. Add 15 grams of USP grade Menthol flakes to the mixture of Step 1.
3. Add 10 grams of USP grade Camphor flakes to the mixture of Step 2. Heat the mixture to ~40° C. to hasten the dissolving of the Camphor flakes while stirring.
4. Add 2 grams of USP grade Liquefied Phenol to the mixture of Step 3.
5. Add 1.8 grams of Nonivamide to the mixture from Step 4. Heat the mixture to 40 to 50° C. to hasten the dissolving of the Nonivamide powder. (Note: Adhere to safety precautions in the handling of the powder.)
6. Allow the solution mixture from Step 5 to cool to room temperature and add 20 grams of Ethyl Alcohol.

Step II—the Addition of Other Ingredients to the Liquid Solution from Step I

Ingredients Include:
The solution mixture from STEP I
17.75 grams of Coconut Oil, Nature's Way EfaGold Coconut Oil, Pure Extra Virgin
Procedure:
1. Add 17.75 grams of Aloe Vera Oil to the mixture from Step I and thoroughly stir the resulting solution mixture. The mixture is now ready for subsequent packaging.

Example 5

Preparation of 100 Grams of the 5.0% Trans-Capsaicin Formulation

Form 7A, Table IIIA

Step I—the Blending of the Ingredients to Produce the 5.0% Capsaicin Formulation Ingredients:
50.0 grams of Methyl Salicylate, Spectrum Chemical, NF, CAS #119-36-8
15.0 grams of Menthol, Crystal, Spectrum Chemical, USP, CAS #2216-51-5
11.0 grams of Camphor, Spectrum Chemical, USP, CAS #76-22-2
1.5 grams of Liquefied Phenol, Spectrum Chemical, CAS #108-95-2
5.0 grams of Trans-Capsaicin Powder, Aversion Technologies, Bowie, Md., USP 30
17.5 grams of Macadamia Nut Oil, Lotioncrafters Lot #1506-3187
Procedure:
1. Add 50.0 grams of NF grade Methyl Salicylate to 250 cc "Pyrex" beaker.
2. Add 15.0 grams of USP grade Menthol Crystals to the Methyl Salicylate in Step 1.
3. Add 11.0 grams of Camphor flakes to the mixture in Step 2.
4. Heat the above mixture to ~50° C. to 60° C. while stirring to hasten the solution of the solid Menthol & Camphor.

5. Add 5.0 grams of Trans-Capsaicin to the heated mixture from Step 5 while gently stirring to solubilize the Trans-Capsaicin.
6. Allow the solution from Step 5 to cool to ~30° C. to 35° C. & then add 1.5 grams of Liquefied Phenol to the solution.
7. Add 17.5 grams of Macadamia Nut Oil to the solution from Step 6 & thoroughly stir.
8. Set aside the mixture & allow it to cool to ambient temperatures.
9. The mixture from Step 8 is now ready for subsequent packaging.

Example 6

Preparation of 100 Grams of the 2.0% Trans-Capsaicin/Apigenin

Form 6A, Table IIIA

Ingredients Include:
9.25 grams of a Super Refined PS80, CRODA, Inc., CAS #9005-65-6
0.75 grams of Apigenin powder, Skyherbs Technologies Co., Lot #0000418019
Procedure:
1. Add 9.25 grams of the highly purified PS80 to a 50 cc "Pyrex" beaker.
2. Add 0.75 grams of Apigenin powder to the PS80.
3. Heat the PS80/Apigenin mixture to a temperature slightly in excess of ~275° C. At about 200° C., the it will be observed that the mixture will take on a light brown/reddish color which will darken when the Apigenin is completely solubilized at ~275° C.
4. The Apigenin/PS80 solution is set aside and allowed to cool to <100° C.

Step II—the Blending of the Ingredients to Produce the 5.0% Capsaicin Formulation Ingredients:
50.0 grams of Methyl Salicylate, Spectrum Chemical, NF, CAS #119-36-8
15.0 grams of Menthol, Crystal, Spectrum Chemical, USP, CAS #2216-51-5
11.0 grams of Camphor, Spectrum Chemical, USP, CAS #76-22-2
1.5 grams of Liquefied Phenol, Spectrum Chemical, CAS #108-95-2
5.0 grams of Trans-Capsaicin Powder, Powder, Aversion Technologies, Bowie, Md., USP 30
17.5 grams of Macadamia Nut Oil, Lotioncrafters Lot #1506-3187
10.0 grams of Apigenin/Polysorbate 80 Concentrate from STEP I.
Procedure:
1. Add 50.0 grams of NF grade Methyl Salicylate to 250 cc "Pyrex" beaker.
2. Add 15.0 grams of USP grade Menthol Crystals to the Methyl Salicylate in Step 1.
3. Add 11.0 grams of Camphor flakes to the mixture in Step 2.
4. Heat the above mixture to ~50° C. to 60° C. while stirring to hasten the solution of the solid Menthol & Camphor.
5. Add 5.0 grams of Trans-Capsaicin to the heated mixture from Step 4 while gently stirring to solubilize the Trans-Capsaicin.
6. Allow the solution from Step 5 to cool to ~30° C. to 35° C. & then add 1.5 grams of Liquefied Phenol to the solution.
7. Add 17.5 grams of Macadamia Nut Oil to the solution from Step 6 & thoroughly stir.
8. Add the 10 grams of the Apigenin/Polysorbate Concentrate from STEP I to the solution from Step 7 and thoroughly stir.
9. Set aside the mixture from Step 8 & allow it to cool to ambient temperatures.
10. The mixture from Step 9 is now ready for subsequent packaging.

Example 7

Preparation of 100 Grams of the 2.0% Trans-Capsaicin/50% Ethyl Alcohol/20.5% Glycerin Formulation Form 3B, Table IIIB Step I—the Blending of the Ingredients to Produce the 5.0% Capsaicin Formulation Ingredients:
50.0 grams of Ethyl Alcohol, Graves Grain Alcohol, 190 Proof
15.0 grams of Menthol, Crystal, Spectrum Chemical, USP, CAS #2216-51-5
11.0 grams of Camphor, Spectrum Chemical, USP, CAS #76-22-2
1.5 grams of Liquefied Phenol, Spectrum Chemical, CAS #108-95-2
2.0 grams of Trans-Capsaicin Powder, Powder, Aversion Technologies, Bowie, Md., USP 30
20.5 grams of Glycerin, Lotioncrafters, USP CAS #56-81-5
Procedure:
1. Add 50.0 grams of Ethyl Alcohol to 250 cc "Pyrex" beaker.
2. Add 15.0 grams of USP grade Menthol Crystals to the Methyl Salicylate in Step 1.
3. Add 11.0 grams of Camphor flakes to the mixture in Step 2.
4. Heat the above mixture to ~40° C. to 50° C. while stirring to hasten the solution of the solid Menthol & Camphor.
5. Add 2.0 grams of Trans-Capsaicin to the heated mixture from Step 5 while gently stirring to solubilize the Trans-Capsaicin.
6. Allow the solution from Step 5 to cool to ~30° C. to 35° C. & then add 1.5 grams of Phenol to the solution.
7. Add 20.5 grams of Glycerin to the solution from Step 6 & thoroughly stir.
8. Set aside the mixture & allow it to cool to ambient temperatures.
9. The mixture from Step 8 is now ready for subsequent packaging.

Example 8

Preparation of 100 Grams of the 2.0% Trans-Capsaicin/50% Methyl Salicylate/20.5% Ethyl Alcohol Formulation Form 9B, Table IIIB Step I—the Blending of the Ingredients to Produce the 5.0% Capsaicin Formulation Ingredients:
50.0 grams of Methyl Salicylate, Spectrum Chemical, NF, CAS #119-36-8
15.0 grams of Menthol, Crystal, Spectrum Chemical, USP, CAS #2216-51-5
11.0 grams of Camphor, Spectrum Chemical, USP, CAS #76-22-2
1.5 grams of Liquefied Phenol, Spectrum Chemical, CAS #108-95-2
2.0 grams of Trans-Capsaicin Powder, Powder, Aversion Technologies, Bowie, Md., USP 30
20.5 grams of Ethyl Alcohol, Graves Grain Alcohol, 190 Proof Procedure:
1. Add 50.0 grams of Methyl Salicylate to 250 cc "Pyrex" beaker.
2. Add 15.0 grams of USP grade Menthol Crystals to the Methyl Salicylate in Step 1.
3. Add 11.0 grams of Camphor flakes to the mixture in Step 2.
4. Heat the above mixture to ~40° C. to 50° C. while stirring to hasten the solution of the solid Menthol & Camphor.
5. Add 2.0 grams of Trans-Capsaicin to the heated mixture from Step 5 while gently stirring to solubilize the Trans-Capsaicin.
6. Allow the solution from Step 5 to cool to ~30° C. to 35° C. & then add 1.5 grams of Phenol to the solution.
7. Add 17.5 grams of Ethyl Alcohol to the solution from Step 6 & thoroughly stir.
8. Set aside the mixture & allow it to cool to ambient temperatures.
9. The mixture from Step 8 is now ready for subsequent packaging.

Example 9

Human Skin Test of Natural Capsaicin, Nonivamide and Trans-Capsaicin Formulations First Test—OTC "CapZasin" and Nonivamide Adult male and female of normal health tested the following formulations:

Formulation #1. OTC "CAPZASIN" containing 0.15% natural capsaicin (in roll-on dispenser)

Formulation #2. OTC "CAPZASIN" 0.10 natural capsaicin (cream)

Formulation #3. 0.25% Nonivamide concentration, Formulation 12, TABLE III (45% methyl salicylate, 15% menthol, 10% camphor, 9.25% PS80, 0.75% apigenin, 10% ethyl alcohol, 7.75% coconut oil)

Formulation #4. 1.8% Nonivamide concentration, Formulation 4, TABLE III, (35% methyl salicylate, 13% menthol, 9% camphor, 9.25% PS80, 0.75% apigenin, 1.5% phenol, 1% alpha bisabolol, 28.7% aloe vera oil)

Subjects applied the above formulations to the topside (dorsal) of the right forearm.

After 30 minutes Subject A reported most S&B from Formulation #1 while Subject B reported most S&B from formulation #2. Subjects A & B reported no S&B, during the first 30 minute period for Formulations #3 & #4.

After 60 minutes Subject A reported most S&B from Formulation #1 while Subject B reported most S&B from formulation #2. Subjects A & B reported no S&B, during the first 60 minute period for Formulations #3 & #4.

After 90 minutes Subject A reported most S&B from Formulation #1 while Subject B reported most S&B from formulation #2. After 90 minutes Subject A reported redness of skin along with S&B from Formulation #1 and redness of skin without S&B from Formulation #4. After 90 minutes Subject B did not report any redness of skin. After 90 minutes Subject A washed off all formulations with rubbing alcohol. While showering 24 hours later, Subject A still felt some S&B from formulation #1.

Both Subjects A & B, using a scale of 1-10 with 10 being the most S&B, reported a maximum level of 2-3 for the above trial during the first 90 minute period for Formulations #1 & #2. Both Subjects A & B reported no S&B, during the first 90 minute period for Formulations #3 & #4.

Subject B did NOT wash off the formulations at all and 12 hours later, still felt some S&B from Formulations #1 & #2. Subject B 12 hours later still felt some S&B from Formulations #1 & #2 at level 3.

After 24 hours, Subject A still felt some S&B from formulations #1 & at level 2. After 24 hours, both Subjects A & B reported no S&B for formulations #3 & #4.

Second Test—Trans-Capsaicin at 5%, 10% and 15%

Formulations 7A, 8A & 9A TABLE IIIA

Same adult male and female subjects of normal health (A and B) also tested the following Trans-Capsaicin formulations (referred to here as "Capsaicin"):

1. 5% Capsaicin concentration (50% methyl salicylate, 15% menthol, 11% camphor, 17.5% macadamia nut oil, 1.5% phenol)
2. 10% Capsaicin concentration (50% methyl salicylate, 15% menthol, 11% camphor, 12.5% macadamia nut oil, 1.5% phenol)
3. 15% Capsaicin concentration (50% methyl salicylate, 15% menthol, 11% camphor, 7.5% macadamia nut oil, 1.5% phenol)

Each subject applied the above formulations to the topside (dorsal) of the left forearm. "Stinging & Burning" sensations (S&B) were rated on a scale of 0 to 10. Erythema (reddening) observations were rated on a scale of 0 to 5 (0 being no erythema):

After 10 Minutes:
Subject A reported:
S&B (stinging and burning) of 1 with a 5% Capsaicin concentration
S&B of 2 with a 10% Capsaicin concentration
S&B of 1 with a 15% Capsaicin concentration
Erythema of 0 (zero) with all three Capsaicin concentrations
Subject B reported:
S&B of 2 with a 5% Capsaicin concentration
S&B of 2 with a 10% Capsaicin concentration
S&B of 2 with a 15% Capsaicin concentration Erythema of 0 (zero) with all three Capsaicin concentrations
After 20 Minutes:
Subject A reported:
S&B of 1 with a 5% Capsaicin concentration
S&B of 2 with a 10% Capsaicin concentration
S&B of 1 with a 15% Capsaicin concentration
Erythema of 0 (zero) with 5% Capsaicin concentration
Erythema of 1 with both 10% & 15% Capsaicin concentrations
Subject B reported:
S&B of 2 with a 5% Capsaicin concentration
S&B of 2 with a 10% Capsaicin concentration
S&B of 2 with a 15% Capsaicin concentration
Erythema of 0 (zero) with all three Capsaicin concentrations
After 30 Minutes:
Subject A reported:
S&B of 0 (zero) with a 5% Capsaicin concentration
S&B of 2 with a 10% Capsaicin concentration
S&B of 1 with a 15% Capsaicin concentration
Erythema of 0 (zero) with 5% Capsaicin concentration
Erythema of 2 with both 10 & 15% Capsaicin concentrations
Subject B reported:
S&B of 2 with a 5% Capsaicin concentration
S&B of 2 with a 10% Capsaicin concentration
S&B of 2 with a 15% Capsaicin concentration
Erythema of 0 (zero) with all three Capsaicin concentrations
After 40 Minutes:
Subject A reported:
S&B of 0 (zero) with a 5% Capsaicin concentration
S&B of 1 with a 10% Capsaicin concentration
S&B of 1 with a 15% Capsaicin concentration
Erythema of 0 (zero) with 5% Capsaicin concentration
Erythema of 2 with both 10 & 15% Capsaicin concentrations
Subject B reported:
S&B of 1 with a 5% Capsaicin concentration
S&B of 1 with a 10% Capsaicin concentration
S&B of 1 with a 15% Capsaicin concentration
Erythema of 0 (zero) with all three Capsaicin concentrations
After 50 Minutes:
Subject A reported:
S&B of 0 (zero) with a 5% Capsaicin concentration
S&B of 0 with a 10% Capsaicin concentration
S&B of 0 with a 15% Capsaicin concentration
Erythema of 0 (zero) with 5% Capsaicin concentration
Erythema of 1 with both 10% & 15% Capsaicin concentrations
Subject B reported:
S&B of 0 with a 5% Capsaicin concentration
S&B of 0 with a 10% Capsaicin concentration
S&B of 0 with a 15% Capsaicin concentration
Erythema 0 (zero) with all three Capsaicin concentrations
After 90 Minutes:
Subject A reported:
S&B of 0 with a 5% Capsaicin concentration
S&B of 1 with a 10% Capsaicin concentration
S&B 0 (zero) with a 15% Capsaicin concentration
Erythema of 0 (zero) with 5% Capsaicin concentration
Erythema of 1 with both 10% & 15% Capsaicin concentrations
Subject B reported:
S&B of 0 (zero) with a 5% Capsaicin concentration
S&B of 0 (zero) with a 10% Capsaicin concentration
S&B of 0 (zero) with a 15% Capsaicin concentration
Erythema 0 (zero) with all three Capsaicin concentrations
After 150 Minutes:
Subject A reported:
S&B of 1 with a 5% Capsaicin concentration
S&B of 2 with a 10% Capsaicin concentration
S&B of 2 with a 15% Capsaicin concentration
Erythema of 0 (zero) with 5% Capsaicin concentration
Erythema 1 with both 10% & 15% Capsaicin concentrations
Subject B reported:
S&B of 2 with a 5% Capsaicin concentration
S&B of 2 with a 10% Capsaicin concentration
S&B of 2 with a 15% Capsaicin concentration
Erythema of 0 (zero) with all three Capsaicin concentrations
After 150 minutes: residual formulations were washed-off the skin using soap and cold water.

Example 10

Human Skin Tests of Nonivamide and Trans-Capsaicin Formulations

Nonivamide Formulation (Formulation 13, Table III)
5% Nonivamide
50-year old male of normal health applied single topical application of 5.0% nonivamide solution (50% methyl salicylate, 15% menthol, 11% camphor, 9.25% PS80, 0.75% apigenin, 6% macadamia nut oil, 2% phenol, 1% alpha bisabolol) for 90 minutes prior to washing off with soap and water.

A single application of formulation via several passes from a roller-ball bottle was made to a 50 cm$^2$ area (7 cm×7 cm) of skin on subject's arm, 20 cm above the elbow joint on the top side of subject's left arm. Stinging and Burning sensations (S&B) were rated on a scale of 0-10. Erythema (reddening) was rates on a scale of 0-5 (0 no erythema).

Subject observed a gradual onset of a slight, but tolerable, burning sensation over the first 20 minutes following application. Maximum irritation (S&B) rated at 2.5 (on a scale of 0 to 10) was observed after 20 minutes. This 2.5 irritation level continued for 20 minutes until the 40-minute mark. From the 40 minute mark to the 60 minute mark, the subject observed a gradual reduction of irritation such that as of the 60 minute mark the irritation level was a 1.5 rating (on a scale of 0 to 10). Complete cessation of irritation had occurred by the 80-minute mark. All levels of irritation were considered to be well within a "tolerable" level for topical use in subject's opinion.

In addition, reddening (erythema) and subsequent cessation of reddening of the entire 50 cm$^2$ application area was observed over the initial 90 minute period of application. Subject observed a reddening rated of a 1 (on a scale of 0 to 5) after 5 minutes, to a rating of 2 after 10 minutes, and a rating of 3 after 15 minutes. The 3 rating was the maximum observed and continued at this level for 25 minutes until the 40 minute mark. Reddening gradually lessened beginning after the 40 minute mark and was completely gone after 70 minutes following application. Reddening was uniform and no blotching or other form of inconsistent effect was observed. By the 20-minute mark, the area of reddening had expanded beyond the 50 cm² application area by 1.5 cm in all directions to encompass a total area of reddening of 72 cm². This was deemed due to the spreading of the formulation over the surface of the skin outside the original application site.

Finalgon—European OTC Product (0.4% Nonivamide)

For comparison purposes, subject applied a European OTC Nonivamide product called Finalgon which contains a Nonivamide concentration of 0.4%. In this application of 0.4% Finalgon subject (50 year old male of normal health) observed a relatively intense burning sensation which was significantly greater than that which occurred with the application of 5.0% Nonivamide of the invention Subject rated the Finalgon-induced burning sensation at a 5 to 6 (on the same scale of 0 to 10) 30 minutes after application. In addition, a more severe form of erythema was experienced on the Finalgon area of application relative to the 5.0% Nonivamide formulation of the invention. Subject rated the Finalgon-induced erythema at a 4 (on the same scale of 0 to 5 used to estimate erythema) 30 minutes after application. Subject believed the S&B and erythema were "intolerable" 30 minutes following application and Finalgon was washed off at that point.

Trans-Capsaicin Formulations

5% Trans-Capsaicin Formulation 7A, Table IIIA

A 50-year old male of normal health applied a single topical application of 5% trans-capsaicin (50% methyl salicylate, 15% menthol, 11% camphor, 17.5% macadamia nut oil, 1.5% phenol) solution for 120 minutes prior to washing off.

Application of the formulation via a 10 ml roller-ball bottle on a 50 cm² (7 cm×7 cm) area of skin arm, 20 cm below the elbow joint on the underside (ventral) of subject's right forearm (a relatively sensitive area of skin). Several passes of the roller-ball were undertaken to cover the entire 50 cm² application area.

Subject observed a gradual onset of a mild, but tolerable, burning sensation over the first 20 minutes following application. This irritation was observed and rated (on a scale of 0-10) to be a 1 after 2 minutes, a 2 after 5 minutes and a 3 after 20 minutes. Maximum irritation rated at a 3 was observed after 20 minutes. This irritation rating of a 3 irritation continued for only 10 minutes until the 30-minute mark. The irritation level had decreased to a rating of 2 by the 40 minute mark. From the 40-minute mark to the 80-minute mark, the subject observed a gradual reduction of irritation, which was observed to be reduced from a 2 rating to a 0.5 rating (on a scale of 0-10) over this period. Complete cessation of irritation occurred at the 120 minute mark. All levels of irritation were considered to be well within a "tolerable" level for topical use in subject's opinion.

In addition, reddening (erythema) and the subsequent cessation of reddening of the entire 50 cm² application area was observed over the initial 90 minute period following application. Subject observed a reddening rated at a 1 (on a scale of 0-5) after 10 minutes, to a rating of 1.5 after 20 minutes, and a rating of 2 after 30 minutes. This reddening rating of 2 was the maximum level observed and lasted from the 30 minute mark until the 60 minute mark. Reddening gradually lessened after the 60-minute mark and was completely gone after 120 minutes following application. Reddening was uniform and no blotching or other form of inconsistent effect was observed. By the 20-minute mark, the area of reddening had expanded beyond the 50 cm² application area by 1.5 cm in all directions to encompass a total area of reddening of 72 cm² due to the spreading of the formulation over the surface of the skin outside of the original application site.

After 20 minutes, the skin area of application became more sensitive to touch. Sensitivity to touch decreased after 60 minutes.

0.1% and 0.15% OTC Product Trans-Capsaicin Formulations

First Test:

For comparison purposes, subject (50 year old male) had previously applied two U.S. OTC products which each contain capsaicin as its active ingredient. These two OTC products were CAPZASIN-HP (containing 0.1% capsaicin) and GELLERT Joint Care (containing 0.17% capsaicin). Products were both creams and were applied to the inner (ventral) side of subject's left arm (a relatively sensitive area of skin). The application of 0.1% CAPZASIN-HP and 0.17% GELLERT Joint Care caused subject a burning sensation which was about the same as that observed for application of 5.0% Trans-Capsaicin. For 0.1% CAPZASIN-HP and GELLERT Joint Care the burning sensation was rated at a 2.5 and a 3 respectively (on the same scale of 0 to 10 used to estimate burning/S&B in 5% Trans-Capsaicin formulation) 30 minutes after application. Subject considered the burning irritation from both U.S. OTC products to be "intense" yet still within a "tolerable" level for topical use. A slight erythema was observed for both U.S. OTC products. Subject rated erythema in both cases at a 1 (on the same scale of 0 to 5 used to estimate erythema) 30 minutes after application.

Second Test:

Subject applied the same two OTC products tested above a second time, but this time on a different area of the skin. CAPZASIN-HP (containing 0.1% capsaicin) and GELLERT Joint Care (containing 0.17% capsaicin) are both creams and were applied to the inner (ventral) side of subject's lower left leg. After 20 minutes CAPZASIN-HP and GELLERT Joint Care had a burning sensation rating of a 1 and a 2, respectively (on the same scale of 0 to 10 used to estimate burning/S&B in 5% Trans-Capsaicin formulation). After 30 minutes each had a burning rating of a 1.5 and 2.5 respectively (the maximum observed for each). From the 30 minute mark to the 90 minute mark both OTC products showed a gradual lessening of the burning sensation such that none was observed by the 90 minute mark in both products. Leg was tanned and no erythema (rating 0) was observed.

10% Trans-Capsaicin Formulation 8A, Table IIIA

A 50-year old male of normal health applied a single topical application of 10% trans-capsaicin ((50% methyl salicylate, 15% menthol, 11% camphor, 12.5% macadamia nut oil, 1.5% phenol)) solution for 120 minutes prior to washing off.

Application of formulation via 10 mg roller-ball bottle was undertaken to achieve an initial dosing on a 50 cm² (7 cm×7 cm) area of skin on his arm, 20 cm below the elbow joint on the underside of his left arm. Several passes of the roller-ball were undertaken to the entire 20 cm² application area.

Subject observed a slight itching a minute after application. Subject noticed a gradual increase in burning sensation over the first 20 minutes until a burning level of 2 (on a scale of 0-10) was observed at the 20 minute mark. The burning sensation remained at a 2 level for 10 minutes until the 30 minute mark. At the 40 minute mark, the burning sensation level had increased to a 2.5, where it remained for 20 minutes until the 60 minute mark. Maximum irritation was rated at a 2.5 (on a scale of 0-10). At the 90-minute mark the burning sensation had dropped to a 2 level. From that point forward subject observed a gradual reduction of irritation. The burning sensation level had decreased to a rating of 1 (on a scale of 0-10) by the 120-minute mark. By the 180-minute mark, the subject noted that the irritation was no more than a 0.5 rating. All levels of irritation were considered to be well within a "tolerable" level for topical use in subject's opinion.

In addition, reddening (erythema) and cessation of reddening of the entire 50 $cm^2$ application area was observed over a 180 minute period following application. Subject observed a reddening rated at 0.5 (on a scale of 0-5) after 10 minutes, to a rating of 1.5 after 20 minutes, a rating of 2.5 after 30 minutes and a rating of 3 after 60 minutes. This reddening rating of 3 was the maximum level. After the 60 minute mark, the reddening gradually lessened and was completely gone after 180 minutes following application. Reddening was uniform and no blotching or other form of inconsistent effect was observed.

By the 20 minute mark, the area of reddening had expanded beyond the 50 $cm^2$ application area by 1.5 cm in all directions to encompass a total area of reddening of 72 $cm^2$.

The area became sensitive to the touch after the 15 minute mark. This sensitivity increased and eventually subsided over time and intensity in a manner that was consistent with the observation of erythema.

10% Trans-Capsaicin Formulation with Ethanol and Methyl Salicylate Formulation 11B, Table IIIB A normally healthy 50-year old male applied a single topical application of a 10% Trans-Capsaicin (50% methyl salicylate, 15% menthol, 11% camphor, 1.5% phenol, 12.5% ethyl alcohol) solution for 80 minutes prior washing off the residual formulation from the application area.

The liquid formulation was applied to a 50 $cm^2$ (7 cm×7 cm) area of skin on the left shoulder via a 10 ml roller-ball bottle. Absorption of the formulation was almost immediate and the area of skin to which formulation was applied was almost dry after one minute, and completely dry after two minutes.

A minute after application, subject noted a slight itching on the application area. Subject noticed a gradual increase in burning sensation over the first 10 minutes. On a scale of (0-10), the subject indicated a burning (S&B) level of 1 at the 10 minute mark. The burning sensation remained relatively constant at a 1 level for the next 40 minutes (i.e., from the 10 to 50 minute mark. At the 60 minute mark the burning sensation had dropped to a 0.5 level. By the 80-minute mark, the subject noted that the irritation was gone, and the recordation was ended. The subject indicated that the maximum irritation (S&B) was rated at a 1.0 (on a scale of 0-10) and that all levels of irritation were considered to be well within a "tolerable" level for topical use in subject's opinion, and in fact hardly noticeable.

Additionally, minimal reddening (erythema) of the entire 50 $cm^2$ application area was observed over the 80 minute duration following application. The subject indicated a reddening level at 0.5 (on a scale of 0-5) after 5 minutes, which gradually increased to a 1.0 after 10 minutes, a 1.5 after 20 minutes. This reddening rating of 1.5 was the maximum level observed. At the 60 minute mark, the reddening had gradually decreased to a level of 0.5, and remained constant at 0.5 when recordation was ended 80 minutes following application. Reddening was uniform and no blotching was observed, The subject observed that the area of erythema did not spread beyond the application area.

Example 11

Treatment of Shoulder Pain with Trans-Capsaicin 0.25% and 2.0% Formulations Formulations 3A & 5A, Table IIIA A 57-year old male of normal health applied multiple topical applications of 0.25% trans-capsaicin (50% methyl salicylate, 15% menthol, 11% camphor, 22.25% macadamia nut oil, 1.5% phenol) solution followed by 2.0% trans-capsaicin solution (50% methyl salicylate, 15% menthol, 11% camphor, 20.5% macadamia nut oil, 1.5% phenol) for the treatment of shoulder pain. Applications of formulation via a 10 ml roller-ball bottle were applied twice daily to the right shoulder. The area of application was ~40 $cm^2$ (5 cm×8 cm) of skin.

The 0.25% trans-capsaicin solution was applied initially twice-a-day for 2 days. The subject experienced no redness (erythema) and no stinging or burning at any time following the four topical applications of the formulation. The subject reported significant relief of shoulder pain but elected to go to a higher concentration of trans-capsaicin for potential increased efficacy.

The 2.0% trans-capsaicin solution was applied twice-a-day for 3 days. The subject experienced no redness (erythema) at any time following the six topical applications of the formulation. Levels of burning and stinging were reported as tolerable. No burning and stinging were experienced immediately (first hours) following application. Two events of moderate burning were experienced: first, on the second day while showering with hot water and then during the third night while sleeping. In both cases the level of burning was tolerable. The subject reported significant relief of shoulder pain and increased mobility and ability to use his right arm.

Example 12

API-CAPS-001: A Randomized, Single-Blind, Multiple Dose Study of the Safety and Tolerability of API-CAPS in Subjects with Osteoarthritis of the Knee Hypothesis/Study Objective The effect of the novel API-CAPS composition is expected to minimize the burning effect of capsaicin following topical application to tolerable levels while the formulation provides pain relief and enhanced joint mobility in the topical treatment of pain associated with osteoarthritis. The objective was to evaluate the efficacy, mobility improvement and tolerability of API-CAPS when applied topically for the treatment of pain from osteoarthritis of the knee. Five concentrations of API-CAPS (0%, 2%, 5%, 10% and 20% w/w trans-capsaicin, USP) were used in this study.

| API-CAPS FORMULATION COMPOSITIONS | | | | | |
|---|---|---|---|---|---|
| INGREDIENTS | 0% (Wt. %) | 2% (Wt. %) | 5% (Wt. %) | 10% (Wt. %) | 20% (Wt. %) |
| TRANS-CAPSAICIN | 0.0 | 2.0 | 5.0 | 10 | 20 |
| ETHYL ALCOHOL | 22.5 | 20.5 | 17.5 | 12.5 | 2.5 |
| METHYL SALICYLATE | 50 | 50 | 50 | 50 | 50 |
| MENTHOL | 15 | 15 | 15 | 15 | 15 |
| CAMPHOR | 11 | 11 | 11 | 11 | 11 |
| PHENOL | 1.5 | 1.5 | 1.5 | 1.5 | 1.5 |
| TOTAL | 100 | 100 | 100 | 100 | 100 |

Study Design

Chronic pain relief resulting from capsaicin is known to be dose dependent and temporary. Topical capsaicin is well tolerated except for a potential acute skin sensation of burning in the area of administration that diminishes over time and with multiple applications. Capsaicin products currently on the market are limited by this acute side effect. API-CAPS formulations were created to minimize potential capsaicin skin burning sensation and efficacious in topical pain treatment.

This was a phase 1, randomized, single-blind, multiple-dose, study of adult subjects with pain from osteoarthritis of the knee, conducted at two investigational centers. Each of the subject's knees (two knees per subject) was separately and randomly assigned in a 1:5 ratio to receive one of five concentrations (0%, 2%, 5%, 10% or 20% capsaicin) of API-CAPS and each knee was individually treated. Study medication was applied once daily to the skin of each knee independently by trained site staff at the investigational study centers for 4 consecutive days. The skin associated with the application site remained uncovered for 60 minutes after API-CAPS was applied. After 60 minutes, the area was cleansed by trained personnel to remove any residual formulation from the surface of the skin. Subjects were not allowed to apply the solution themselves or take the medication home. Subjects were instructed to avoid exposing the treated skin to any form of heat (hot water, vigorous exercise, direct sunlight, heating pad, etc.) until 24 hours after their final API-CAPS treatment. Subjects were also told not to apply any topical substances to the treated skin area and to avoid wearing tight clothing at the site of application during this time. If the subject experienced intolerable pain or severe irritation from the study medication after they left the clinic, they were allowed to apply cold water, ice, or a cold pack, and they were allowed to also take oral pain medications to ease the pain. All evaluations were performed at the study sites. Each subject signed an Informed Consent Form and had all questions answered before any study procedures were performed.

Study Data

Thirty subjects were enrolled and treated in this study. Of the 30 enrolled subjects, nine did not complete the full 4 applications per the protocol. Of these nine subjects: five discontinued the study in connection with Adverse Events and four did not return for unnamed reasons. Adverse events consisted of coughing deemed "possibly" or "probably" related to the study, resulting from multiple subjects treated with formulations on both knees utilizing the same small poorly ventilated waiting room at one or both sites. One subject, MTR, reported using oral medication for pain of burning. All Adverse Events were resolved.

Rating of Osteoarthritis (OA) Pain: the level of Osteoarthritis (OA) Pain was assessed (rated) by all subjects prior to each application and recorded by trained professionals. Data utilized here were those Osteoarthritis (OA) Pain ratings recorded prior to initiation of treatment and those prior to the fourth application of one of five API-CAPS formulations to both knees of each subject. Ratings utilized included those from all 21 patients receiving 4 applications and two receiving 2 and 3 applications respectively (23 total subjects). Subjects rated the current Osteoarthritis (OA) Pain in their joints on a 0-10 numeric pain rating scale (0=no pain; 10=worst pain imaginable) in conjunction with the Wong-Baker Faces Rating Scale as a guide. Additionally, subjects were asked whether their Osteoarthritis (OA) Pain was "Better", "Same" or "Worse" than prior to the $2^{nd}$, $3^{rd}$ and $4^{th}$ applications.

Tolerability Assessment (current burning skin sensation): the burning sensation on the skin was assessed (rated) by all subjects following each application and recorded by trained professionals. Data utilized here were those burning sensation ratings recorded at 15, 30, 45, and 60 minutes following each application of one of the five API-CAPS formulations to both knees of each subject. Tolerability ratings utilized included all 21 patients receiving 4 applications and two receiving 2 and 3 applications respectively (23 total subjects). At each time interval subjects rated the current burning sensation on a 0-10 numeric rating scale (0=no pain; 10=worst pain imaginable) in conjunction with the Wong-Baker Faces Rating Scale as a guide.

Mobility Assessment (enhanced joint mobility): mobility in the treated joints was assessed by all subjects prior to each application and recorded by trained professionals. Data utilized here were those mobility assessments recorded prior to each application of one of five API-CAPS formulations to both knees of each subject. Assessments utilized included those from all 21 patients receiving 4 applications and two receiving 2 and 3 applications respectively (23 total subjects). Subjects were asked whether their "ability to use the joint" was "Better", "Same" or "Worse" than pre-treatment levels prior to the $2^{nd}$, $3^{rd}$ and $4^{th}$ applications.

Results

Efficacy of API-CAPS Treatment

The summary of percent improvement in Osteoarthritic (OA) Pain prior to initiation of short-term treatment are shown in the following Table.

| PAIN REDUCTION AS A FUNCTION OF CAPSAICIN CONCENTRATION (Based on the pain reduction from the $1^{st}$ visit to the follow-up visit at end of study) | | |
| --- | --- | --- |
| CAPSAICIN CONCENTRATION (Wt. %) | NUMBER OF KNEES TREATED | PAIN REDUCTION (%) |
| 0 | 12 | 100 |
| 2 | 8 | 100 |
| 5 | 8 | 100 |
| 10 | 10 | 88[1] |
| 20 | 8 | 100 |

Note:
[1] One subject experienced a 40% pain reduction level for both knees

Tolerability of API-CAPS Treatment

The combined API-CAPS tolerability for the right and left knees for capsaicin concentrations of 0%, 2%, 5%, 10%, and 20% are shown in FIG. 1. The tolerability readings are considered well within the range of what would be considered "tolerable" therapy for the treatment of osteoarthritis pain.

Figure 2:
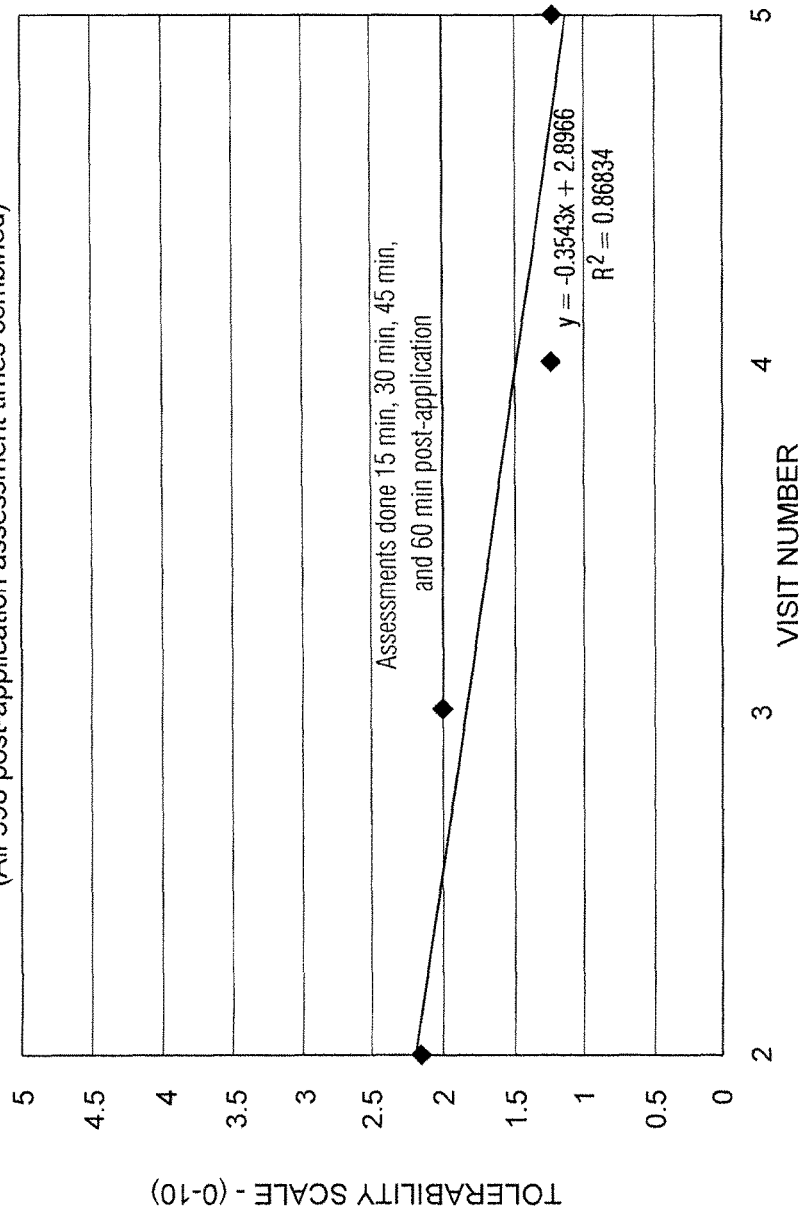
FIG. 2 is a plot of the tolerability of API-CAPS (0%, 2%, 5%, 10% or 20% capsaicin) following once daily, 60 minute exposure, treatment of osteoarthritic knees for 4 consecutive days. Subjects rated tolerability (burning & stinging sensation) at 15, 30, 45, and 60 minutes after API-CAPS application on a 0-10 numeric rating scale (0=no pain; 10=worst pain imaginable) in conjunction with the Wong-Baker Faces Rating Scale as a guide.

The summary of the tolerability of API-CAPS treatment over the course of the four days of treatment at 15, 30, 45 and 60 minutes following each application are shown in FIG. 2.

Conclusions

Topical API-CAPS treatment of osteoarthritis pain was very effective. The reduction in Osteoarthritis (OA) Pain was dramatic. The percent improvement in osteoarthritis pain prior to the $4^{th}$ dose ranged from >45% to 100% from initial osteoarthritis pain levels prior to initiation of this short-term course of therapy. At the follow-up visit at the end of study the percent improvement in osteoarthritis pain ranged from 88% to 100%. There was a trend for greater efficacy in mitigation of osteoarthritis pain with increasing capsaicin concentration when comparing responses to treatment of left versus right contralateral knees with different capsaicin concentrations in the same patient. When asked whether their Osteoarthritis (OA) Pain was "Better", "Same" or "Worse" prior to the $2^{nd}$, $3^{rd}$ and $4^{th}$ applications, subjects replied "better" in 122 out of 123 replies, with one recording "worse".

Topical API-CAPS treatment in this study was demonstrated to be highly tolerable as evidenced in the graphics above. At each concentration level of one of five API-CAPS formulations, subjects rated their burning sensations to be overwhelmingly either non-existent or well within a range of tolerability. Tolerability ratings averaged 2.2 upon the first application, 1.3 after the fourth application and trended down over time. The literature on topical capsaicin tolerability clearly teaches that different people sense a potential transient burning sensation to capsaicin to different degrees and that this sensation can vary from one exposure to the next. This is evident in our findings. In this study, capsaicin tolerability was, in general, found to be dose (capsaicin-concentration) dependent; with the 20% capsaicin concentration having the greater incidence of tolerability values ranging above 6 and the frequency of burning and stinging sensations decreased following repetitive treatments. At capsaicin concentrations below 20% tolerability readings typically ranged from 0 to 6 and are considered well within the range of what would be considered "tolerable" therapy for the treatment of osteoarthritis pain.

Example 13

API-CAPS-004: 0.25% API-CAPS Topical Treatment for Osteoarthritis Pain in Hands and Knees of Adult Patients Hypothesis/Study Objective The effect of the novel API-CAPS composition is expected to minimize the burning effect of capsaicin following topical application to tolerable levels while the formulation provides pain relief and enhanced joint mobility in the topical treatment of pain associated with osteoarthritis. The objective was to evaluate the efficacy, mobility improvement and tolerability of 0.25% API-CAPS when applied topically for the treatment of pain from osteoarthritis of the hand and knee.

| API-CAPS Formulation Composition | |
|---|---|
| INGREDIENTS | 0.25% (Wt. %) |
| TRANS-CAPSAICIN | 0.25 |
| ETHYL ALCOHOL | 22.25 |
| METHYL SALICYLATE | 50 |
| MENTHOL | 15 |
| CAMPHOR | 11 |
| PHENOL | 1.5 |
| TOTAL | 100 |

Study Design

Chronic pain relief resulting from capsaicin is known to be dose dependent and temporary. Topical capsaicin is well tolerated except for a potential acute skin sensation of burning in the area of administration which diminishes over time and with multiple applications. Capsaicin products currently on the market are limited by this acute side effect. API-CAPS was created to minimize potential capsaicin skin burning sensation and be efficacious in topical pain treatment.

This was a multiple-dose study of adult subjects with pain from osteoarthritis of the hand and knee, conducted at two investigational sites API-CAPS was applied three times per day, five days per week, for two weeks to the skin of the afflicted hand or knee by trained site staff. The skin associated with the application site remained uncovered for 60 minutes after API-CAPS was applied. After 60 minutes, the area was cleansed by trained personnel to remove any residual formulation from the surface of the skin. Subjects were then instructed to avoid exposing the treated skin to any form of heat (hot water, vigorous exercise, direct sunlight, etc.) for 24 hours. Subjects were also told not to apply any topical substances to the treated skin area and to avoid wearing tight clothing at the site of application during this time. If the subject experienced intolerable pain or severe irritation from the study medication after they left the clinic, they were allowed to apply cold water, ice, or a cold pack. All evaluations were performed at the study sites. Each subject signed an Informed Consent Form and had all questions answered before any study procedures were performed. Subjects were not allowed to apply the solution themselves or take the medication home.

Study Data

Sixty-one subjects were enrolled in this study. Fifty-seven subjects completed the study. Of the 61 enrolled subjects, four did not return for personal reasons. No treatment related adverse events were reported.

Rating of Osteoarthritis (OA) Pain: the level of Osteoarthritis (OA) Pain was assessed (rated) by all subjects prior to each application and recorded by trained professionals. Arthritis pain was rated on a 0-10 numeric scale (0=no pain; 10=worst pain imaginable) using the Wong-Baker Faces Rating Scale as a guide. If the patient had bilateral pain and both sides were treated and data for each side (right and left) was collected independently. Initial OA pain level data were collected at either day 1 or day 2. The first value recorded for pain level was used in the subsequent analysis of percent pain reduction achieved at the end of study.

Tolerability Assessment (current burning skin sensation): the burning sensation on the skin was assessed (rated) by all subjects before treatment with API-CAPS and just prior to washing the skin area (60 minutes after medication application) and recorded by trained professionals. The subjects rated the current burning sensation on a 0-10 numeric rating scale (0=no pain; 10=worst pain imaginable) in conjunction with the Wong-Baker Faces Rating Scale as a guide.

Mobility Assessment (enhanced joint mobility): mobility in the treated joints was assessed by all subjects prior to each application and recorded by trained professionals. Subjects were asked whether their "ability to use the joint" was "Better", "Same" or "Worse" than pre-treatment levels prior to the starting treatment.

Results

Efficacy of API-CAPS Treatment

Figure 3:
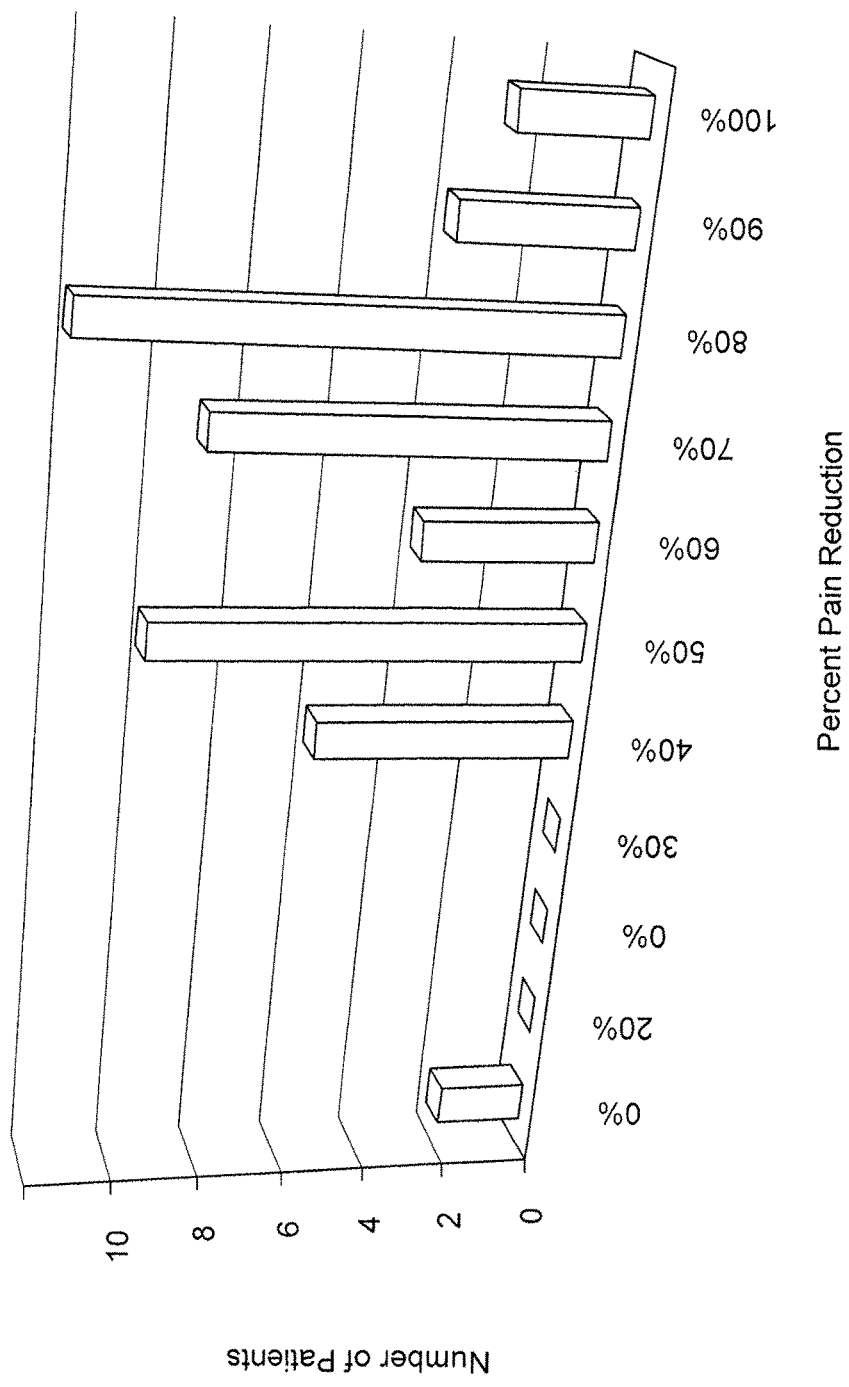
FIG. 3 shows the end of study percent pain reduction from initial osteoarthritic pain level prior to initiation of short-term API-CAPS, 0.25% capsaicin, therapy (two weeks of treatment applied three times per day, five days per week).

FIG. 3 shows the summary of end of study percent improvement in Osteoarthritic (OA) Pain with short-term treatment (two weeks of treatment applied three times per day, five days per week).

Tolerability of API-CAPS Treatment

Figure 4:
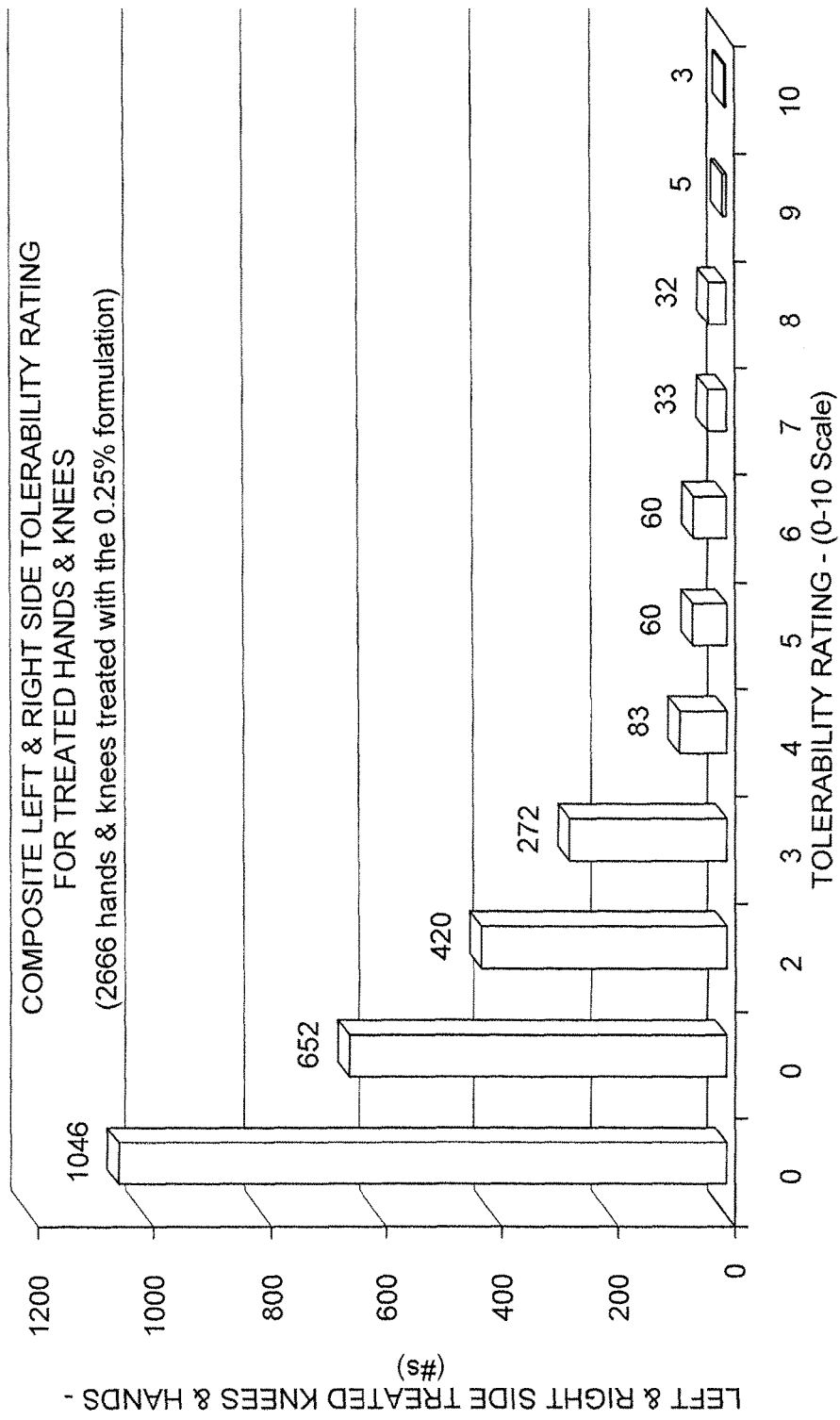
FIG. 4 is a bar chart graph displaying the tolerability of API-CAPS, 0.25% capsaicin, treatment following each application over the course of two weeks of treatment applied three times per day, five days per week. Subjects rated tolerability (burning sensation) on a 0-10 numeric rating scale (0=no pain; 10=worst pain imaginable) in conjunction with the Wong-Baker Faces Rating Scale as a guide.
Figure 5:
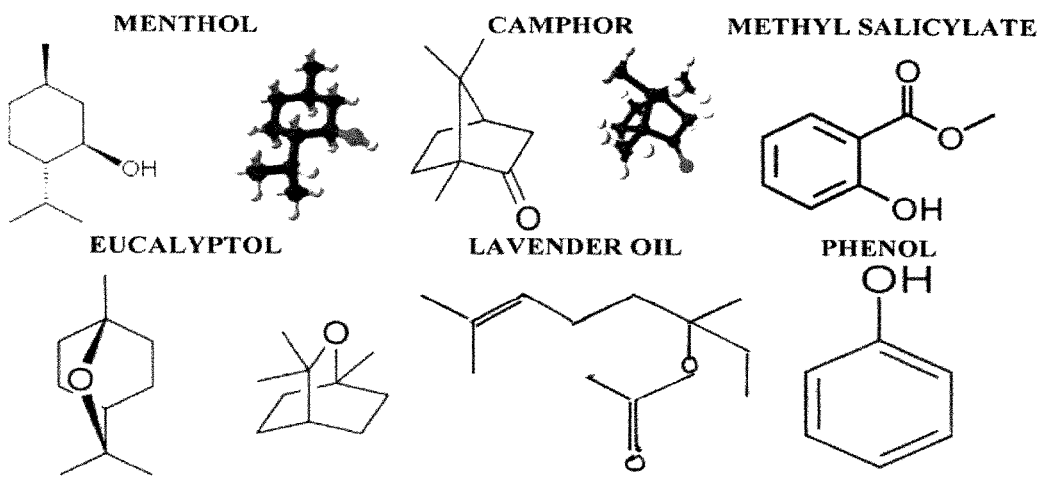
FIG. 5 shows the molecular structures of selected analgesic ingredients: menthol, camphor, methyl salicylate, eucalyptol, lavender oil, and phenol.

A summary of the tolerability of API-CAPS treatment following each application over the course of two weeks of treatment applied three times per day, five days per week is shown in FIG. 4.

Conclusions

Topical API-CAPS treatment of osteoarthritis pain was very effective as evidenced by the graphics above. The percent improvement in osteoarthritis pain at the end of study ranged from 0% to 100% from initial osteoarthritis pain levels prior to initiation of this short-term course of therapy; with almost all subjects achieving >40% reduction in pain.

Topical API-CAPS treatment in this study was demonstrated to be highly tolerable as evidenced in the graphics above. The literature on topical capsaicin tolerability clearly teaches that different people sense a potential transient burning sensation to capsaicin to different degrees and that this sensation can vary from one exposure to the next. This is evident in our findings. In this study, capsaicin tolerability was, in general, found to be excellent; with most subjects reporting no burning and the preponderance tolerability values well below 6. These tolerability values are considered well within the range of what would be considered "tolerable" therapy for the treatment of osteoarthritis pain. Topical API-CAPS treatment in this study was also demonstrated to enhance mobility, presumably due to the dramatic decrease in Osteoarthritis (OA) Pain. When asked whether their mobility was "Better", "Same" or "Worse" prior to each applications, subjects replied "better" in 2313 cases, the "same" in 50 cases, and "worse" in only one case.

Example 14

API-CAPS-005: Multiple Dose Case Studies of Treatment with API-CAPS for Pain from Osteoarthritis in the Elderly Hypothesis/Study Objective The effect of the novel API-CAPS composition is expected to minimize the burning effect of capsaicin following topical application to tolerable levels while the formulation provides efficacy in the topical treatment of pain associated with osteoarthritis. The objective was to evaluate the efficacy and tolerability of API-CAPS when applied topically for the treatment of pain from osteoarthritis in the elderly. Three concentrations of API-CAPS (2%, 5%, and 10% w/w trans-capsaicin, USP) were available to the Investigators for use in this study.

| API-CAPS FORMULATION COMPOSITIONS | | | |
|---|---|---|---|
| INGREDIENTS | 2% (Wt. %) | 5% (Wt. %) | 10% (Wt. %) |
| TRANS-CAPSAICIN | 2.0 | 5.0 | 10 |
| ETHYL ALCOHOL | 20.5 | 17.5 | 12.5 |
| METHYL SALICYLATE | 50 | 50 | 50 |
| MENTHOL | 15 | 15 | 15 |
| CAMPHOR | 11 | 11 | 11 |
| PHENOL | 1.5 | 1.5 | 1.5 |
| TOTAL | 100 | 100 | 100 |

Study Design

Chronic pain relief resulting from capsaicin is known to be dose dependent and temporary. Topical capsaicin is well tolerated except for a potential acute skin sensation of burning in the area of administration which diminishes over time and with multiple applications. Capsaicin products currently on the market are limited by this acute side effect. API-CAPS was created to minimize this burning skin sensation.

The Investigators identified eight subjects who could benefit from treatment with API-CAPS and who meet standard eligibility criteria. Each subject signed an Informed Consent Form (ICF) prior to treatment with API-CAPS. For each subject, one joint was topically treated 5 times with the same strength of API-CAPS, with one application each day. API-CAPS was applied to the same joint each time, and the concentration was not increased or decreased. The clinician administered API-CAPS. The skin associated with the application site remained uncovered for 60 minutes after API-CAPS was applied. After 60 minutes, the area was cleansed by trained personnel to remove any residual formulation from the surface of the skin. Subjects were not allowed to apply the solution themselves or take the medication home. Subjects were instructed to avoid exposing the treated skin to any form of heat (hot water, vigorous exercise, direct sunlight, heating pad, etc.) until 24 hours after their final API-CAPS treatment. Subjects were also told not to apply any topical substances to the treated skin area and to avoid wearing tight clothing at the site of application during this time. If the subject experienced intolerable pain or severe irritation from the study medication after they left the clinic, they may apply cold water, ice, or a cold pack, and they may also take oral pain medications to ease the pain.

The Investigator consulted with each of the eight subjects to determine the proper concentration for treatment (2%, 5%, and 10% API-CAPS). The Investigator considered the severity of osteoarthritis pain, the subject's capacity for tolerating a burning skin sensation (potential side effect), and the area of skin where the medication would be applied (target skin area). The 10% concentration was considered most appropriate for subjects with chronic osteoarthritis of long duration who have exhausted other options. Rating of Osteoarthritis (OA) Pain: Prior to each medication treatment, subjects rated the current pain in their joint from osteoarthritis on a 0-10 numeric pain rating scale (0=no pain; 10=worst pain imaginable) in conjunction with the Wong-Baker Faces Rating Scale as a guide.

Tolerability Assessment (current burning skin sensation): Burning skin sensation was assessed by the patient just prior to treatment, at 30 minutes after API-CAPS application, and at 60 minutes post-application on a 0-10 numeric rating scale (0=no pain; 10=worst pain imaginable) in conjunction with the Wong-Baker Faces Rating Scale as a guide.

Results

Efficacy of API-CAPS Treatment

A measure of osteoarthritic pain at the start of the study (prior to first treatment) and at the end of the study for each of the eight subjects is summarized in the following Tables.

| % PAIN LEVEL REDUCTION DOSING WITH API-CAPS | | | | | | | | |
|---|---|---|---|---|---|---|---|---|
| | Capsaicin Concentration (%) | | | | | | | |
| | 2 | 2 | 5 | 5 | 5 | 5 | 10 | 10 |
| | Subject Initials | | | | | | | |
| | MDC | VE | AV | DJ | ES | MR | AAR | CD |
| Start Pain Level (0-10 Scale) | 3 | 4 | 6 | 7 | 7 | 10 | 6 | 10 |
| End Pain Level (0-10 Scale) | 2 | 0 | 4 | 0 | 4 | 4 | 0 | 3 |

-continued

% PAIN LEVEL REDUCTION DOSING WITH API-CAPS

| | Capsaicin Concentration (%) | | | | | | |
|---|---|---|---|---|---|---|---|
| | 2 | 2 | 5 | 5 | 5 | 5 | 10 | 10 |
| | Subject Initials | | | | | | | |
| | MDC | VE | AV | DJ | ES | MR | AAR | CD |
| Pain Level Change | 1 | 4 | 2 | 7 | 3 | 6 | 6 | 7 |
| Pain Level Reduction (%) | 33 | 100 | 33 | 100 | 43 | 60 | 100 | 70 |

AVERAGE TOLERABILITY SCORE (0-10 Scale)

| Patient Group | Treatment Times - (Minutes) | | |
|---|---|---|---|
| (All Patients) | 0 | 30 | 60 |
| All Visits | NA | 3.35 | 3.07 |
| Days 2-6 | 1.24 | 3.41 | 3.31 |
| Day 1 | 0.00 | 3.00 | 2.38 |
| Day 2 | 0.50 | 0.25 | 0.75 |
| Day 3 | | | |
| Day 4 | 3.00 | 3.50 | 4.13 |
| Day 5 | 0.67 | 6.25 | 5.14 |
| Day 6 | 0.00 | 4.00 | 2.00 |

Conclusions

Topical API-CAPS treatment of osteoarthritis pain was very effective; percent improvement in osteoarthritis pain at the end of study ranged from 33% to 100% from initial osteoarthritis pain levels prior to initiation of this short-term course of therapy.

The literature on topical capsaicin tolerability clearly teaches that different people sense a potential transient burning sensation to capsaicin to different degrees and that this sensation can vary from one exposure to the next. This is evident in our findings. Six out of eight subjects (75%) participating in this study generally encountered burning sensations at levels considered to be "tolerable" (6 and below). However, two of the eight subjects (25%) experienced individual tolerability readings as high as 9 or 10 at several reading points during the study. Both subjects of these extreme cases occurred with the application of the 5% concentration. Averaging tolerability ratings of these two highly sensitive subjects into the tolerability data set raises the overall tolerability averages significantly. The median values of the tolerability readings ranged from 0 to 6 and are considered well within the range of what would be considered "tolerable" therapy for the treatment of osteoarthritis pain.

Example 15

Components Elimination Comparison

Two individuals took place in a trial designed to explore the differences in the capsaicin burning sensation caused by the elimination of one or more individual components from the embodiment of the invention including menthol camphor and phenol. Subject #1 (50 year old healthy male) applied six (6) distinct capsaicin formulations on six (6) separate areas of skin on his thighs (3 per leg). Each application site was approximately 20 cm$^2$ (5 cm×4 cm) in area.

Subject #2 (39 year old healthy female) applied the same six (6) distinct capsaicin formulations simultaneously on six (6) separate areas of skin on her inner left arm (above and below the inside crease of the elbow joint). Each application site was approximately 8 cm$^2$ (2 cm×4 cm) in area. Both areas are considered to be relatively sensitive areas of skin and as such were chosen in order to distinguish differences in burning sensations as much as possible. The formulations applied are presented below:

APPLIED FORMULATIONS

| | 10% MA | | No Menthol | | No Camphor | | No Phenol | | No Phenol, Camphor, Menthol w/Mac Oil | | No Phenol, Camphor, Menthol w/EtOH | |
|---|---|---|---|---|---|---|---|---|---|---|---|---|
| | Sub j1 | Sub j2 | Sub j1 | Sub j2 | Sub j1 | Sub j2 | Sub j1 | Sub j2 | Sub j1 | Sub j2 | Sub j1 | Sub j2 |
| Capsaicin | 10 | 10 | 5 | 5 | 5 | 5 | 5 | 5 | 5 | 5 | 5 | 5 |
| Methyl Salicate | 50 | 50 | 50 | 50 | 50 | 50 | 50 | 50 | 50 | 50 | 50 | 50 |
| Ethyl Alcohol | 12.5 | 12.5 | 32.5 | 32.5 | 28.5 | 28.5 | 19 | 19 | 0 | 0 | 45 | 45 |
| Menthol | 15 | 15 | 0 | 0 | 15 | 15 | 0 | 0 | 0 | 0 | 0 | 0 |
| Camphor | 11 | 11 | 11 | 11 | 0 | 0 | 15 | 15 | 0 | 0 | 0 | 0 |
| Phenol | 1.5 | 1.5 | 1.5 | 1.5 | 1.5 | 1.5 | 11 | 11 | 0 | 0 | 0 | 0 |
| Macadamia Nut Oil | 0 | 0 | 0 | 0 | 0 | 0 | 0 | 0 | 45 | 45 | 0 | 0 |

Note that three of the six formulations eliminates one single compound respectively (menthol, camphor or phenol) amongst the various combinations of compounds comprising the inventive compositions. The other two formulations are variations which exclude all three of these compounds: menthol, camphor and phenol. The 6$^{th}$ formulation applied is 10% capsaicin formulation with none of the active components removed. The six (6) formulations were all applied upon each subject within 2 minutes of one another. At the time increments of 5, 10, 15, 20, 30, 45, 60, 90 and 120 the levels of the burning sensation were taken for all application sites and rated on a scale of 1-10. Relative comparisons between application sites were facilitated dramatically by the simultaneous application of formulations. Each application site was rated on a scale of 1-10 for the burning sensation at each time interval.

Erythema reddening was also rated (measured by eye) at the same time increments for all six (6) application sites. Relative comparisons between applications sites were facilitated by the simultaneous application of formulations. At each time increment, erythema was rated on a scale of (1-5).

Burning Sensation Results

| | FORMULATIONS | | | | | |
|---|---|---|---|---|---|---|
| TIME AFTER DOSING (minutes) | 10% Cap MA | 5% CAP MA no Menthol | 5% CAP MA no Camphor | 5% CAP MA No Phenol | 5% CAP No PhCaMe w/Mac Nut Oil | 5% CAP No PhCaMe w/EtOH |
| Subject #1 | | | | | | |
| 5 | 0.5 | 1.0 | 1.0 | 1.0 | 1.5 | 1.5 |
| 10 | 0.5 | 1.0 | 1.0 | 1.5 | 1.5 | 1.5 |
| 15 | 0.5 | 1.0 | 1.5 | 1.5 | 2.0 | 2.0 |
| 20 | 1.0 | 1.5 | 1.5 | 2.0 | 2.5 | 3.0 |
| 30 | 1.5 | 2.0 | 1.5 | 2.0 | 3.0 | 3.5 |
| 45 | 1.5 | 2.5 | 2.0 | 2.0 | 3.5 | 3.5 |
| 60 | 1.0 | 2.5 | 2.0 | 2.0 | 3.0 | 3.0 |
| 75 | 1.0 | 2.5 | 2.0 | 2.5 | 2.5 | 2.5 |
| 90 | 1.0 | 2.5 | 2.0 | 2.5 | 2.5 | 2.5 |
| 120 | 1.0 | 2.5 | 2.0 | 2.5 | 2.5 | 2.0 |
| Subject #2 | | | | | | |
| 5 | 0.0 | 0.5 | 0.0 | 0.5 | 0.0 | 0.0 |
| 10 | 0.0 | 1.0 | 0.0 | 2.0 | 0.0 | 0.5 |
| 15 | 0.0 | 2.0 | 1.0 | 2.0 | 0.0 | 1.0 |
| 20 | 0.0 | 2.0 | 1.0 | 1.0 | 1.0 | 1.5 |
| 30 | 0.0 | 2.0 | 1.0 | 1.0 | 1.0 | 1.5 |
| 45 | 0.0 | 2.5 | 0.0 | 1.0 | 1.0 | 1.0 |
| 60 | 0.0 | 2.5 | 0.0 | 1.0 | 1.0 | 0.0 |
| 75 | 0.0 | 2.5 | 0.0 | 0.0 | 2.0 | 0.0 |
| 90 | 0.0 | 2.5 | 0.0 | 0.0 | 2.0 | 0.0 |
| 120 | 0.0 | 2.5 | 0.0 | 0.0 | 1.0 | 0.0 |

Erythema Results

| | FORMULATIONS | | | | | |
|---|---|---|---|---|---|---|
| TIME AFTER DOSING (minutes) | 10% Cap MA | 5% CAP MA no Menthol | 5% CAP MA no Camphor | 5% CAP MA No Phenol | 5% CAP No PhCaMe w/Mac Nut Oil | 5% CAP No PhCaMe w/EtOH |
| Subject #1 | | | | | | |
| 5 | 0.5 | 1.0 | 1.0 | 1.0 | 1.5 | 1.5 |
| 10 | 0.5 | 1.0 | 1.0 | 1.5 | 1.5 | 1.5 |
| 15 | 0.5 | 1.0 | 1.5 | 1.5 | 2.0 | 2.0 |
| 20 | 1.0 | 1.5 | 1.5 | 2.0 | 2.5 | 3.0 |
| 30 | 1.5 | 2.0 | 1.5 | 2.0 | 3.0 | 3.5 |
| 45 | 1.5 | 2.5 | 2.0 | 2.0 | 3.5 | 3.5 |
| 60 | 1.0 | 2.5 | 2.0 | 2.0 | 3.0 | 3.0 |
| 75 | 1.0 | 2.5 | 2.0 | 2.5 | 2.5 | 2.5 |
| 90 | 1.0 | 2.5 | 2.0 | 2.5 | 2.5 | 2.5 |
| 120 | 1.0 | 2.5 | 2.0 | 2.5 | 2.5 | 2.0 |
| Subject #2 | | | | | | |
| 5 | 0.0 | 0.0 | 0.0 | 0.0 | 0.0 | 0.0 |
| 10 | 0.5 | 2.0 | 0.5 | 1.0 | 0.5 | 0.5 |
| 15 | 0.5 | 2.5 | 0.5 | 1.0 | 0.5 | 1.0 |
| 20 | 0.0 | 2.5 | 0.5 | 2.0 | 1.0 | 1.0 |
| 30 | 0.0 | 2.5 | 0.5 | 2.0 | 1.0 | 0.5 |
| 45 | 0.0 | 2.5 | 1.0 | 2.0 | 2.0 | 0.0 |
| 60 | 0.0 | 2.5 | 1.0 | 2.0 | 2.0 | 0.0 |
| 75 | 0.0 | 2.5 | 0.0 | 1.0 | 2.0 | 0.0 |
| 90 | 0.0 | 2.5 | 0.0 | 0.0 | 2.0 | 0.0 |
| 120 | 0.0 | 2.5 | 0.0 | 0.0 | 1.0 | 0.0 |

Example 16

API-CAPS-002, Cohort 1: 0.25% API-CAPS (0.25% w/w Trans-Capsaicin, USP) & Capzasin HP Arthritis Pain Relief Analgesic Cream (0.1% Capsaicin)

Hypothesis/Study Objective

The effect of the novel API-CAPS composition is expected to minimize the burning effect of capsaicin following topical application to tolerable levels. The objective of this study was to assess the tolerability of 0.25% API-CAPS (0.25% w/w Trans-Capsaicin, USP) compared to Capzasin HP Arthritis Pain Relief Analgesic Cream (0.1% Capsaicin).

API-CAPS Formulation Composition

| INGREDIENTS | 0.25 (Wt. %) |
|---|---|
| TRANS-CAPSAICIN | 0.25 |
| ETHYL ALCOHOL | 22.25 |
| METHYL SALICYLATE | 50 |
| MENTHOL | 15 |
| CAMPHOR | 11 |
| PHENOL | 1.5 |
| TOTAL | 100 |

Study Design

This was a single-blind, single dose, over-the-counter (OTC) product marketing study in 12 adult healthy volunteers, conducted at a single study center. Test Materials consist of 0.25% API-CAPS (0.25% w/w Trans-Capsaicin, USP) compared to Capzasin HP Arthritis Pain Relief Analgesic Cream (0.1% Capsaicin). These two Test Materials were applied to contralateral sites on the subject's back by the site staff following subject's signed Informed Consent Form after having all questions answered before any study procedures may be performed. The screening procedures established eligibility for study participation, and included demographics, height, weight, vital signs, medical history, brief physical exam (optional), and evaluation of inclusion and exclusion criteria.

Subjects were instructed to shower or bathe the evening before or morning of Treatment. Each of the two contralateral areas of Test Material application were 49 square centimeters (7×7 cm); just below the right and left shoulder blades on the subject's back. The Test Materials were applied randomly to one side or the other of the back (right or left).

The subjects evaluated tolerability prior to dosing, one minute after dosing, and every 15 minutes post-dose for 2 hours. Tolerability was measured by the subject's evaluation of a skin sensation of burning on a 0-10 Numeric Rating Scale (where 0 is no sensation and 10 is very severe burning, i.e., worst pain imaginable) using the Wong-Baker faces as a guide.

Skin irritation (dermatologic evaluation) was assessed by a trained clinical evaluator prior to dosing, and at 30 minutes, 1 hour, and 2 hours post-dose using a standard 0 to 7 rating scale (where 0 is no evidence of irritation and 7 is a strong reaction spreading beyond test site). The same evaluator performed all assessments for a subject.

After completion of the 2-hour post-dose evaluations, the site staff cleansed the subject's back to remove any residual product and subjects were instructed to avoid exposing their back to any form of heat (hot water, vigorous exercise, direct sunlight, etc.) for 24 hours. Subjects were released from the clinic and instructed to contact the study staff if they had any adverse experiences that are potentially related to the Test Materials.

Results

| Subjective Assessments (Burning) | | |
|---|---|---|
| | 0.25% API-CAPS (0.25% w/w Trans-Capsaicin, USP) | Capzasin HP Arthritis Pain Relief Analgesic Cream (0.1% Capsaicin) |
| N = | 12 | 12 |
| Mean | 0.11 | 0.10 |
| Std Dev | 0.21 | 0.20 |
| Median | 0.00 | 0.00 |
| Range | 0.00-0.70 | 0.00-0.50 |
| Paired t-test | P = 0.9279 | |

| Dermatologic Evaluations | | |
|---|---|---|
| | 0.25% API-CAPS (0.25% w/w Trans-Capsaicin, USP) | Capzasin HP Arthritis Pain Relief Analgesic Cream (0.1% Capsaicin) |
| N = | 12 | 12 |
| Mean | 0.33 | 0.31 |
| Std Dev | 0.22 | 0.50 |
| Median | 0.25 | 0.00 |
| Range | 0.00-0.75 | 0.00-1.5 |
| Paired t-test | P = 0.8977 | |

Conclusions

Both 0.25% API-CAPS (0.25% w/w Trans-Capsaicin, USP) and Capzasin HP Arthritis Pain Relief Analgesic Cream (0.1% Capsaicin) are comparable (p≥0.05) and very tolerable with respect to potential capsaicin-induced burning as well as comparable (p≥0.05) and very tolerable in potential skin irritation.

API-CAPS-002, Cohort 2: 0.25% API-CAPS (0.25% w/w Trans-Capsaicin, USP) & Capzasin No-Mess Applicator (0.15% Capsaicin)

Hypothesis/Study Objective

The effect of the novel API-CAPS vehicle is expected to minimize the burning effect of 0.25% capsaicin following topical application to tolerable levels. The objective of this study was to assess the tolerability of 0.25% API-CAPS (0.25% w/w Trans-Capsaicin, USP) compared to Capzasin No-Mess Applicator (0.15% Capsaicin).

| API-CAPS Formulation Composition | |
|---|---|
| INGREDIENTS | 0.25 (Wt. %) |
| TRANS-CAPSAICIN | 0.25 |
| ETHYL ALCOHOL | 22.25 |
| METHYL SALICYLATE | 50 |
| MENTHOL | 15 |
| CAMPHOR | 11 |
| PHENOL | 1.5 |
| TOTAL | 100 |

Study Design

This was a single-blind, single dose, over-the-counter (OTC) product marketing study in 12 adult healthy volunteers, conducted at a single study center. Test Materials consist of 0.25% API-CAPS (0.25% w/w Trans-Capsaicin, USP) compared to Capzasin No-Mess Applicator (0.15% Capsaicin). These two Test Materials were applied to contralateral sites on the subject's back by the site staff following subject's signed Informed Consent Form after having all questions answered before any study procedures may be performed. The screening procedures established eligibility for study participation, and included demographics, height, weight, vital signs, medical history, brief physical exam (optional), and evaluation of inclusion and exclusion criteria.

Subjects were instructed to shower or bathe the evening before or morning of Treatment. Each of the two contralateral areas of Test Material application were 49 square centimeters (7×7 cm); just below the right and left shoulder blades on the subject's back. The Test Materials were applied randomly to one side or the other of the back (right or left).

The subjects evaluated tolerability prior to dosing, one minute after dosing, and every 15 minutes post-dose for 2 hours. Tolerability was measured by the subject's evaluation of a skin sensation of burning on a 0-10 Numeric Rating Scale (where 0 is no sensation and 10 is very severe burning, i.e., worst pain imaginable) using the Wong-Baker faces as a guide.

Skin irritation (dermatologic evaluation) was assessed by a trained clinical evaluator prior to dosing, and at 30 minutes, 1 hour, and 2 hours post-dose using a standard 0 to 7 rating scale (where 0 is no evidence of irritation and 7 is a strong reaction spreading beyond test site). The same evaluator performed all assessments for a subject.

After completion of the 2-hour post-dose evaluations, the site staff cleansed the subject's back to remove any residual product and subjects were instructed to avoid exposing their back to any form of heat (hot water, vigorous exercise, direct sunlight, etc.) for 24 hours. Subjects were released from the clinic and instructed to contact the study staff if they had any adverse experiences that are potentially related to the Test Materials.

Results

| Subjective Assessments (Burning) | | |
|---|---|---|
| | 0.25% API-CAPS (0.25% w/w Trans-Capsaicin, USP) | Capzasin HP Arthritis Pain Relief Analgesic Cream (0.1% Capsaicin) |
| N = | 12 | 12 |
| Mean | 0.55 | 0.01 |
| Std Dev | 0.94 | 0.03 |
| Median | 0.2 | 0.00 |
| Range | 0.00-3.40 | 0.00-0.10 |
| Paired t-test | P = 0.0739 | |

| Dermatologic Evaluations | | |
|---|---|---|
| | 0.25% API-CAPS (0.25% w/w Trans-Capsaicin, USP) | Capzasin HP Arthritis Pain Relief Analgesic Cream (0.1% Capsaicin) |
| N = | 12 | 12 |
| Mean | 0.21 | 0.00 |
| Std Dev | 0.28 | 0.00 |
| Median | 0.13 | 0.00 |
| Range | 0.00-0.75 | 0.00-0.00 |
| Paired t-test | P = 0.0172 | |

Conclusions

Both 0.25% API-CAPS (0.25% w/w Trans-Capsaicin, USP) and Capzasin No-Mess Applicator (0.15% Capsaicin) are comparable (p≥0.05) and very tolerable with respect to potential capsaicin-induced burning as well as very tolerable in potential skin irritation.

Example 17

Diclofenac Solubility Studies

Experimental Solubility Procedures and Results

All solubility samples were prepared in 20 gram sample size. The ingredients of each test samples were weighed to the nearest 0.01 grams. The 20 gram samples were mixed in 50 cc Pyrex glass beakers.

All solubility studies were performed with "Diclofenac Sodium Salt" obtained from Sigma Aldrich, St. Louis, Mo. (CAS #15307-79-6; Sigma-Aldrich Catalog No. D6899; Lot # BCBB7312; M.P. 275-277° C.)

The molecular structure of Diclofenac Sodium is shown below:

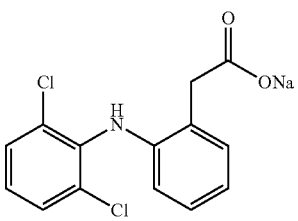

The ingredients were thoroughly mixed at ambient temperatures ranging from 75° F. to 80° F.

The solvents that indicated little or negligible solubility levels of diclofenac sodium at room temperature were heated to about 35° C. to determine if the increased temperature would impact the solubility of the diclofenac sodium. However, the elevated temperature level of ~35° C. did not have a significant impact in increasing the diclofenac sodium in those mixtures where the diclofenac solubility levels were "sparingly soluble to insoluble".

| SAMPLE NUMBER | SOLVENT/SOLVENT MIXTURES | DICLOFENAC SODIUM SOLUBILITY |
|---|---|---|
| 1 | 98 wt. % [1]Methyl Salicylate, 2 wt. % [9]Diclofenac Sodium | Sparingly Soluble/Insoluble |
| 2 | 50 wt. % [1]Methyl Salicylate, 15 wt. % [2]Menthol, 11 wt. % [3]Camphor, 1.5 wt. % [4]Phenol, 20.5 wt. % [5]Macadamia Nut Oil, 2 wt. % [9]Diclofenac Sodium | Sparingly Soluble/Insoluble |
| 3 | 98 wt. % [6]Ethyl Alcohol, 2 wt. % [9]Diclofenac Sodium | [10]Completely Soluble |
| 4 | 98 wt. % [7]Transcutol, 2 wt. % Diclofenac Sodium | [10]Completely Soluble |
| 5 | 88 wt. % Methyl Salicylate, 10 wt. % Ethyl Alcohol, 2 wt. % [9]Diclofenac Sodium | [10]Completely Soluble |
| 6 | 50 wt. % Methyl Salicylate, 15 wt. % Menthol, 11 wt. % Camphor, 1.5 wt. % Phenol, 18.5 wt. % Macadamia Nut Oil, 2 wt. % [9]Diclofenac Sodium | Sparingly Soluble/Insoluble |
| 7 | 50 wt. % Methyl Salicylate, 15 wt. % Menthol, 11 wt. % Camphor, 1.5 wt. % Phenol, 18.5 wt. % Ethyl Alcohol, 2 wt. % [8]Capsaicin, 2 wt. % [9]Diclofenac Sodium | [10]Completely Soluble |
| 8 | 50 wt. % Methyl Salicylate, 15 wt. % Menthol, 11 wt. % Camphor, 1.5 wt. % Phenol, 10.5 wt. % Ethyl Alcohol, 2 wt. % [8]Capsaicin, 2 wt. % [9]Diclofenac Sodium | [10]Completely Soluble |

NOTE:
[1]Methyl Salicylate, Spectrum Chemical, NF, CAS # 119-36-8
[2]L-Menthol, Crystal, Spectrum Chemical, USP, CAS # 2216-51-5
[3]Camphor, Synthetic, Spectrum Chemical, USP, CAS # 76-22-2
[4]Phenol, Liquefied (Carbolic Acid), USP, Spectrum Chemical, CA 108-95-2
[5]Macadamia Nut Oil, Lotioncrafters Lot # 1506-3187, CAS #128497-20-1
[6]Ethyl Alcohol, Graves Grain Alcohol, 190 Proof
[7]Transcutol™, (Ethoxydiglycol), Lotioncrafters, Lot# CAS # 111-90-0
[8]Trans-Capsaicin, Aversion Technologies Inc., 95.7% Trans-Capsaicin, Balance Cis-Capsaicin, USP 30, CAS # 404-86-4
[9]Diclofenac Sodium, Lot # BCBB7312, Sigma-Aldrich Catalog No. D6899, CAS # 15307-79-6
[10]Samples 3, 4, 5 & 7 were placed in sealed 16 cc Pyrex vials and placed in a freezer maintained at ~5° F. for 48 hours. There was no visible evidence of any precipitates formed. Further, no visible evidence of precipitation, was observed after >5 days at ambient conditions. All solutions were totally transparent & all mixtures completely miscible.

The table below includes the compositions of 7 completely miscible and transparent diclofenac sodium and capsaicin liquid solutions that were prepared.

The Composition of the Miscible Liquid Solution

| INGREDIENTS | SAMPLE NUMBER | | | | | | |
|---|---|---|---|---|---|---|---|
| | 1 (wt. %) | 2 (wt. %) | 3 (wt. %) | 4 (wt. %) | 5 (wt. %) | 6 (wt. %) | 7 (wt. %) |
| [1]CAPSAICIN | 0 | 2 | 2 | 0.25 | 2 | 5 | 10 |
| [2]DICLOFENAC SODIUM | 2 | 2 | 2 | 1.5 | 1.5 | 1.5 | 1.5 |
| [3]METHYL SALICYATE | 0 | 50 | 50 | 50 | 50 | 50 | 50 |
| [4]MENTHOL | 0 | 15 | 15 | 15 | 15 | 15 | 15 |

-continued

The Composition of the Miscible Liquid Solution

| INGREDIENTS | SAMPLE NUMBER | | | | | | |
|---|---|---|---|---|---|---|---|
| | 1 (wt. %) | 2 (wt. %) | 3 (wt. %) | 4 (wt. %) | 5 (wt. %) | 6 (wt. %) | 7 (wt. %) |
| (5)CAMPHOR | 0 | 11 | 11 | 11 | 11 | 11 | 11 |
| (6)PHENOL | 0 | 1.5 | 1.5 | 1.5 | 1.5 | 1.5 | 1.5 |
| (7)ETHYL ALCOHOL | 20 | 0 | 18.5 | 20.75 | 19 | 16 | 11 |
| (8)MACADAMIA NUT OIL | 78 | 10.5 | 0 | 0 | 0 | 0 | 0 |
| (9)TRANSCUTOL | 0 | 8 | 0 | 0 | 0 | 0 | 0 |

NOTE:
(1)Trans-Capsaicin, Aversion Technologies Inc., 95.7% Trans-Capsaicin, Balance Cis-Capsaicin, USP 30, CAS # 404-86-4
(2)Diclofenac Sodium, Sigma-Aldrich Catalog No. D6899; Lot # BCBB7312, CAS # 15307-79-6
(3)Methyl Salicylate, Spectrum Chemical, NF, CAS # 119-36-8
(4)L-Menthol, Crystal, Spectrum Chemical, USP, CAS # 2216-51-5
(5)Camphor, Synthetic, Spectrum Chemical, USP, CAS # 76-22-2
(6)Phenol, Liquefied (Carbolic Acid), USP, Spectrum Chemical, CA 108-95-2
(7)Ethyl Alcohol, Graves Grain Alcohol, 190 Proof
(8)Macadamia Nut Oil, Lotioncrafters Lot # 1506-3187, CAS #128497-20-1
(9)Transcutol, (Ethoxydiglycol), Lotioncrafters, Lot# Lot# 034A00429324-3426, CAS #111-90-0)

It is evident that alcohols (ethyl alcohol and/or ethoxydiglycol) are required to effect the solubility of Diclofenac salts within the oil based ingredients of the capsaicin vehicles. Significantly, as noted in Sample 5 of the table above, an ethyl alcohol content of 10% results in the complete solution of 2% Diclofenac Sodium within in a liquid solution containing 88% methyl salicylate. Total solubility/miscibility of this 2% Diclofenac sodium solution was observed after exposure to 5° F. (−15° C.) for 48 hours. Formulations with ethyl alcohol concentration >10 wt. % will result in the solubility of higher diclofenac salt concentrations.

Based on the results of the aforementioned solubility experiments, it was concluded that the ethyl alcohol capsaicin vehicle was capable of maintaining complete solubility/miscibility with concentrations of <2 wt. % Diclofenac Sodium salts.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

All documents and other information sources cited herein are hereby incorporated in their entirety by reference.

What is claimed is:

1. A composition comprising:
   i) 2-30% by weight of a capsaicinoid, and
   ii) 50-95% by weight of an analgesic agent comprising a) a topical salicylate and b) a TRPM8 agonist, capable of solubilizing said capsaicinoid,
   wherein said topical salicylate solubilizes said capsaicinoid, and wherein said composition comprises an amount of analgesic agent sufficient to eliminate or reduce the burning or stinging sensation or erythema created by the topical administration of the capsaicinoid to a mammal,
   wherein the composition is in a form selected the group consisting of sprays, gels, emulsions, and mixtures thereof, and
   wherein said TRPM8 agonist is icilin or eucalyptol.

2. The composition as claimed in claim 1, wherein said analgesic agent comprises the topical salicylate, the TRPM8 agonist, and a TRPV3 agonist.

3. The composition as claimed in claim 1, wherein said composition is a gel.

4. The composition as claimed in claim 1, wherein said capsaicinoid is capsaicin.

5. The composition as claimed in claim 1, wherein said capsaicinoid is trans-capsaicin or nonivamide.

6. The composition as claimed in claim 1, wherein said TRPM8 agonist is eucalyptol.

7. The composition as claimed in claim 2, wherein the TRPV3 agonist is camphor.

8. The composition as claimed in claim 1, wherein said analgesic agent comprises i) methyl salicylate and ii) at least one of menthol, camphor and phenol.

9. The composition as claimed in claim 1, wherein said composition further comprises an alcohol.

10. The composition as claimed in claim 1, wherein said composition comprises:
    2-30% by weight of a capsaicinoid,
    30-70% by weight methyl salicylate,
    1-20% by weight menthol, and
    1-20% by weight camphor,
    wherein the percentage by weight of the methyl salicylate, menthol, and camphor is greater than 50% of the composition.

11. The composition as claimed in claim 1, wherein said composition comprises:
    2-30% by weight of a capsaicinoid,
    30-75% by weight methyl salicylate and ethanol,
    1-20% by weight menthol, and
    1-20% by weight camphor,
    wherein the percentage by weight of the methyl salicylate, menthol, and camphor is greater than 50% of the composition.

12. The composition as claimed in claim 1, wherein said composition comprises:
2-30% by weight of a capsaicinoid,
40-75% by weight methyl salicylate,
10-25% ethanol,
10-20% by weight menthol, and
10-20% by weight camphor.

13. The composition as claimed in claim 1, wherein said composition comprises:
2-30% by weight of capsaicin,
40-75% by weight methyl salicylate
10-25% ethanol,
10-20% by weight menthol,
10-20% by weight camphor, and
0.5-5% phenol.

14. The composition as claimed in claim 11, wherein said composition further comprises glycerol.

15. The composition as claimed in claim 14, wherein said composition is a gel.

16. The composition as claimed in claim 1, wherein said composition further comprises an anti-inflammatory agent.

17. The composition as claimed in claim 1, wherein said composition further comprises a surfactant.

18. The composition as claimed in claim 1, wherein said composition further comprises an NSAID.

19. The composition as claimed in claim 18, wherein the NSAID is selected from the group consisting of aspirin, ibuprofen, naproxen, ketoprofen, and diclofenac.

20. The composition as claimed in claim 1, wherein said composition further comprises an odor reducing agent.

21. The composition as claimed in claim 1, wherein said composition further comprises phenol.

22. The composition as claimed in claim 11, wherein said composition further comprises phenol.

23. A composition comprising:
2-30% by weight of a capsaicinoid,
icilin or eucalyptol,
methyl salicylate and ethyl alcohol, and
phenol,
wherein said methyl salicylate and ethyl alcohol solubilize said capsaicinoid,
wherein the percentage by weight of the methyl salicylate and phenol is greater than 50% of the composition, and
wherein the composition is in a form selected the group consisting of sprays, gels, emulsions, and mixtures thereof.

24. The composition as claimed in claim 23, wherein said composition comprises:
2-30% by weight of a capsaicinoid compound,
30-75% by weight methyl salicylate and ethyl alcohol, and
0.5-5% phenol.

25. A composition comprising:
2-30% by weight of a capsaicinoid,
70-95% by weight of an analgesic agent comprising a topical salicylate, and
icilin or eucalyptol,
wherein said topical salicylate solubilizes said capsaicinoid, and
wherein said composition comprises an amount of analgesic agent sufficient to eliminate or reduce the burning or stinging sensation or erythema created by the topical administration of the capsaicinoid to a mammal,
wherein said composition does not include turpentine oil, and
wherein the composition is in a form selected the group consisting of sprays, gels, emulsions, and mixtures thereof.

26. The composition as claimed in claim 25, wherein said analgesic agent comprises a topical salicylate and a TRPM8 agonist.

27. The composition as claimed in claim 25, wherein the composition is a gel.

28. The composition as claimed in claim 25, wherein said analgesic agent is i) methyl salicylate and ii) at least one of menthol, camphor and phenol.

29. The composition as claimed in claim 25, wherein said composition further comprises an alcohol.

30. The composition as claimed in claim 26 wherein said composition further comprises a TPRV3 agonist.

31. The composition as claimed in claim 27, wherein said gel comprises capsaicin, methyl salicylate, camphor and menthol.

* * * * *